(12) United States Patent
Ingber et al.

(10) Patent No.: US 9,951,313 B2
(45) Date of Patent: Apr. 24, 2018

(54) METHODS AND USES FOR EX VIVO TISSUE CULTURE SYSTEMS

(75) Inventors: Donald E. Ingber, Boston, MA (US); Yusuke Torisawa, Kyoto (JP); Geraldine Hamilton, Cambridge, MA (US); Akiko Mammoto, Brookline, MA (US); Tadanori Mammoto, Brookline, MA (US); Catherine Spina, Boston, MA (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 311 days.

(21) Appl. No.: 14/122,273

(22) PCT Filed: May 31, 2012

(86) PCT No.: PCT/US2012/040188
§ 371 (c)(1),
(2), (4) Date: Mar. 7, 2014

(87) PCT Pub. No.: WO2012/166903
PCT Pub. Date: Dec. 6, 2012

(65) Prior Publication Data
US 2014/0186414 A1  Jul. 3, 2014

Related U.S. Application Data

(60) Provisional application No. 61/492,609, filed on Jun. 2, 2011, provisional application No. 61/601,745, filed on Feb. 22, 2012.

(51) Int. Cl.
*C12N 5/077* (2010.01)
*A01N 1/02* (2006.01)
(Continued)

(52) U.S. Cl.
CPC ......... *C12N 5/0669* (2013.01); *A01N 1/0247* (2013.01); *A61K 35/28* (2013.01); *G01N 27/44791* (2013.01)

(58) Field of Classification Search
CPC .. C12N 5/0673; C12N 5/0669; A01N 1/0247; A61K 35/28
(Continued)

(56) References Cited

U.S. PATENT DOCUMENTS

2006/0166354 A1   7/2006  Wikswo et al.
2011/0003303 A1*  1/2011  Pagano ............ B01L 3/502761
                                                  435/6.19

(Continued)

FOREIGN PATENT DOCUMENTS

EA    200601901 A1   4/2007
JP    2011/092065 A  5/2011
(Continued)

OTHER PUBLICATIONS

Legasse et al. (2000). Purified hematopoietic stem cells can differentiate into hepatocytes in vivo. Nature Medicine, v6(11), p. 1229-1234.*

(Continued)

*Primary Examiner* — Sean C. Barron
(74) *Attorney, Agent, or Firm* — Nixon Peabody LLP; David S. Resnick; Nicole D. Kling

(57) ABSTRACT

The technology described herein is directed to methods and devices that can be used to induce functional organ structures to form within an implantation device by implanting it in vivo within the body of a living animal, and allowing cells and tissues to impregnate the implantation device and establish normal microenvironmental architecture and tissue-tissue interfaces. Then the contained cells and tissues can be surgically removed intact and either transplanted into (Continued)

another animal or maintained ex vivo by perfusing it through one or more of the fluid channels with medium and/or gases necessary for cell survival.

18 Claims, 29 Drawing Sheets

(51) Int. Cl.
*A61K 35/28* (2015.01)
*G01N 27/447* (2006.01)

(58) Field of Classification Search
USPC .......................................................... 435/325
See application file for complete search history.

(56) References Cited

U.S. PATENT DOCUMENTS

| | | |
|---|---|---|
| 2011/0033887 A1 | 2/2011 | Fang et al. |
| 2011/0104803 A1 | 5/2011 | Tamai et al. |
| 2011/0250585 A1 | 10/2011 | Ingber et al. |

FOREIGN PATENT DOCUMENTS

| | | |
|---|---|---|
| RU | 2275913 C2 | 5/2006 |
| RU | 2301677 C1 | 6/2007 |
| WO | 2009/133943 A1 | 11/2009 |
| WO | 2010/144745 A2 | 12/2010 |
| WO | 2011/046884 A2 | 4/2011 |

OTHER PUBLICATIONS

Giarratana et al. (2005). Ex vivo generation of fully mature human red blood cells from hematopoietic stem cells. Nature Biotechnology, v23, p. 69-74.*

Kirshner et al. A unique three-dimensional model for evaluating the impact of therapy on multiple myeloma. Blood (2008), v112(7), p. 2935-2945.*

Vukicevic et al. Identification of multiple active growth factors in basement membrane Matrigel suggests caution in interpretation of cellular activity related to extracellular matrix components. Exp Cell Res (1992), v202(1), p. 1-8; Abstract only.*

Panoskaltsis et al. Engineering a Mimicry of Bone Marrow Tissue Ex Vivo. Journal of Bioscience and Bioengineering (2005), v100(1), p. 28-35. (Year: 2005).*

Warnke et al., Growth and transplantation of a custom vascularized bone graft in a man, The Lancet, 364 (9436):766-770 (Aug. 28, 2004).

Chubenko, Internet Journal of commercial biotechnology Retrieved from the Internet, URL: http://www.cbio.ru/page/47/id/2670/ (In Russian and machine translation to English), Journal version published in "Poplar Mechanics", #6-2006. "Engineers of human bodies".

Kiselev et al., Priroda (Nature), 10:1-10 (2006). "Human Embryo Stem Cells" Retrieve from the Internet, URL: http://vivovoco.rsl.ru/VV/JOURNAL/NATURE/10_06/CELLS.HTM.

Uss et al., "Cryopreservation of Human Cells" Retrieved from the Internet, URL: http://bmp.onego.ru/ru/project.php?id=1, Meditsinskaya Panorama Journal, 2(27):38, (2003).

Boitano et al., "Aryl Hydrocarbon Receptor Antagonists Promote the Expansion of Human Hematopoietic Stem Cells", Science 329: 1345-348 (Sep. 10, 2010).

Cook et al., "Micromarrows-Three-Dimensional Coculture of Hematopoietic Stem Cells and Mesenchymal Stromal Cells", Tissue Engineering, Part C (vol. 18), No. 5; 319-328 (2012).

Csaszar et al., "Rapid Expansion of Human Hematopoietic Stem Cells", Cell Stem Cell, (10):218-229 (Feb. 3, 2012).

Dimaggio, et al., "Toward modeling the bone marrow niche using scaffold-based 3D culture systems", Biomaterials, (32):321-329 (2011).

Nichols, et al., "In vitro analog of human bone marrow from 3D scaffolds with biomimetic inverted colloidal crystal geometry", Biomaterials, (30):1071-1079 (2009).

Takagi, "Cell Processing for Ex-Vivo Expansion of Hematopoietic Cells", Journal of Bioscience and Bioengineering, vol. 99(3): 189-196 (2005).

Toh et al., "A novel 3D mammalian cell perfusion-culture system in microfludic channels", Lab on a Chip, 7:302-309 (2007).

Torikai et al., Journal of Thoracic and Cardiovascular Surgery, 136:37-45 (2008). "A self-renewing, tissue-engineered vascular graft for arterial reconstruction."

Vincentelli et al., Journal of Thoracic and Cardiovascular Surgery,134:424-432 (2007). "In vivo autologous recellularization of a tissue-engineered heart valve: Ar bone marrow mesenchymal stem cells the best candidates?".

Mikos et al., Biotechnology and Bioengineering, 42:716-723 (1993). "Prevascularization of porous biodegradable polymers."

Wojciechowski et al., British Journal of Hematology,140:673-681 (2008). "Capture and Enrichment of CD34-Positive Haematopoietic Stem and Progenitor Cells From Blood Circulation Using P-Selectin in an Implantable Device."

Daniel et al., "Multi-reservoir device for detecting a soluble cancer biomarker", Lab Chip, 7(10):1288-1293 (2007).

Domachuk et al., "Bio-microfluidics: Biomaterials and Biomimetic Designs", Adv. Mater., 22(2):249-260 (2010).

Kelleher et al., "Engineering extracellular matrix through nanotechnology", J. R. Soc. Interface, 7 Suppl 6:S717-S729 (2010).

Sim et al., "A pneumatic micro cell chip for the differentiation of human mesenchymal stem cells under mechanical stimulation", Lab Chip, 7(12):1775-1782 (2007).

Giarratana et al., "Ex vivo generation of fully mature human red blood cells from hematopoietic stem cells", Nature Biotechnology 23(1):69-74 (2005).

Devine et al., "Clinical application of hematopoietic progenitor cell expansion: current status and future prospects", Bone Marrow Transplantation 31(4):241-252 (2003).

Glowacki et al. "Demineralized bone implants", Clinics in Plastic Surgery 12(2):233-241 (1985).

Luo et al. "Enhanced bone regeneration around dental implant with bone morphogenetic protein 2 gene and vascular endothelial growth factor protein delivery", Clinical Oral Implants Research 23(4):467-473 (2012).

* cited by examiner

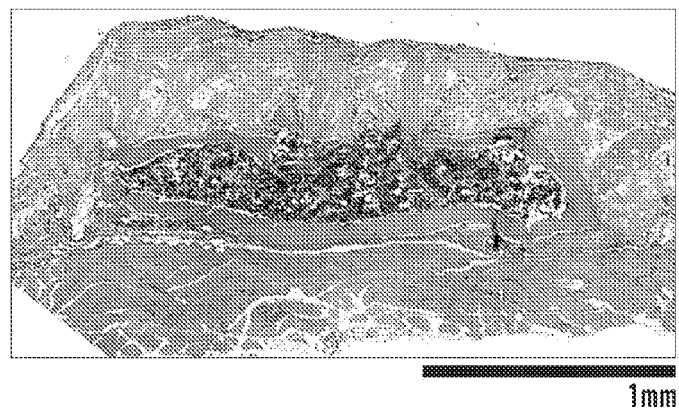
FIG. 6A
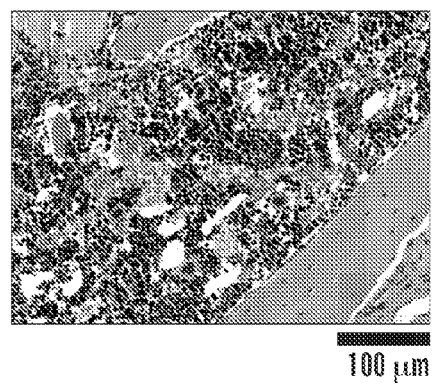 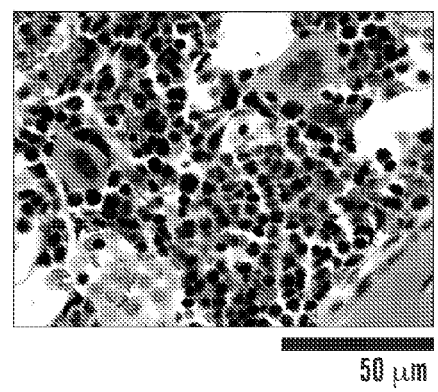
FIG. 6B      FIG. 6C

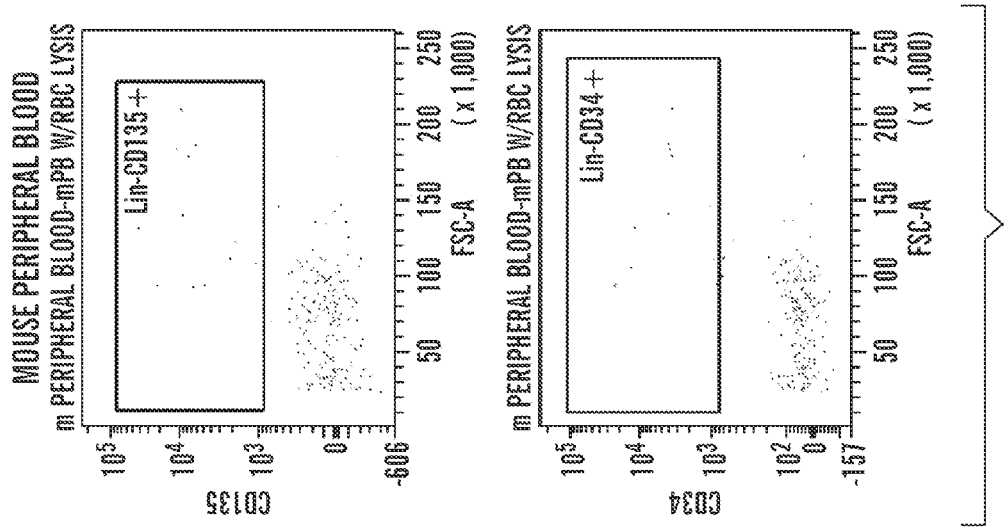
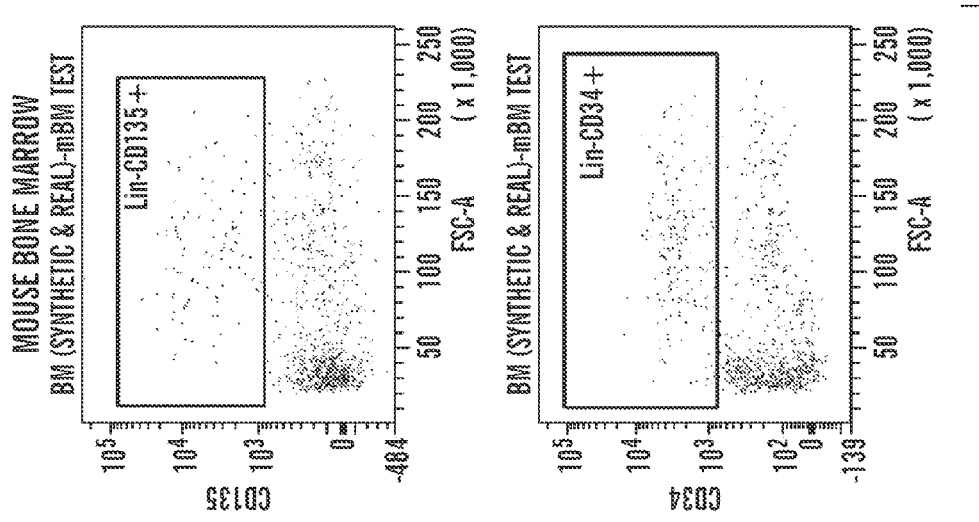
FIG. 10A
FIG. 10B

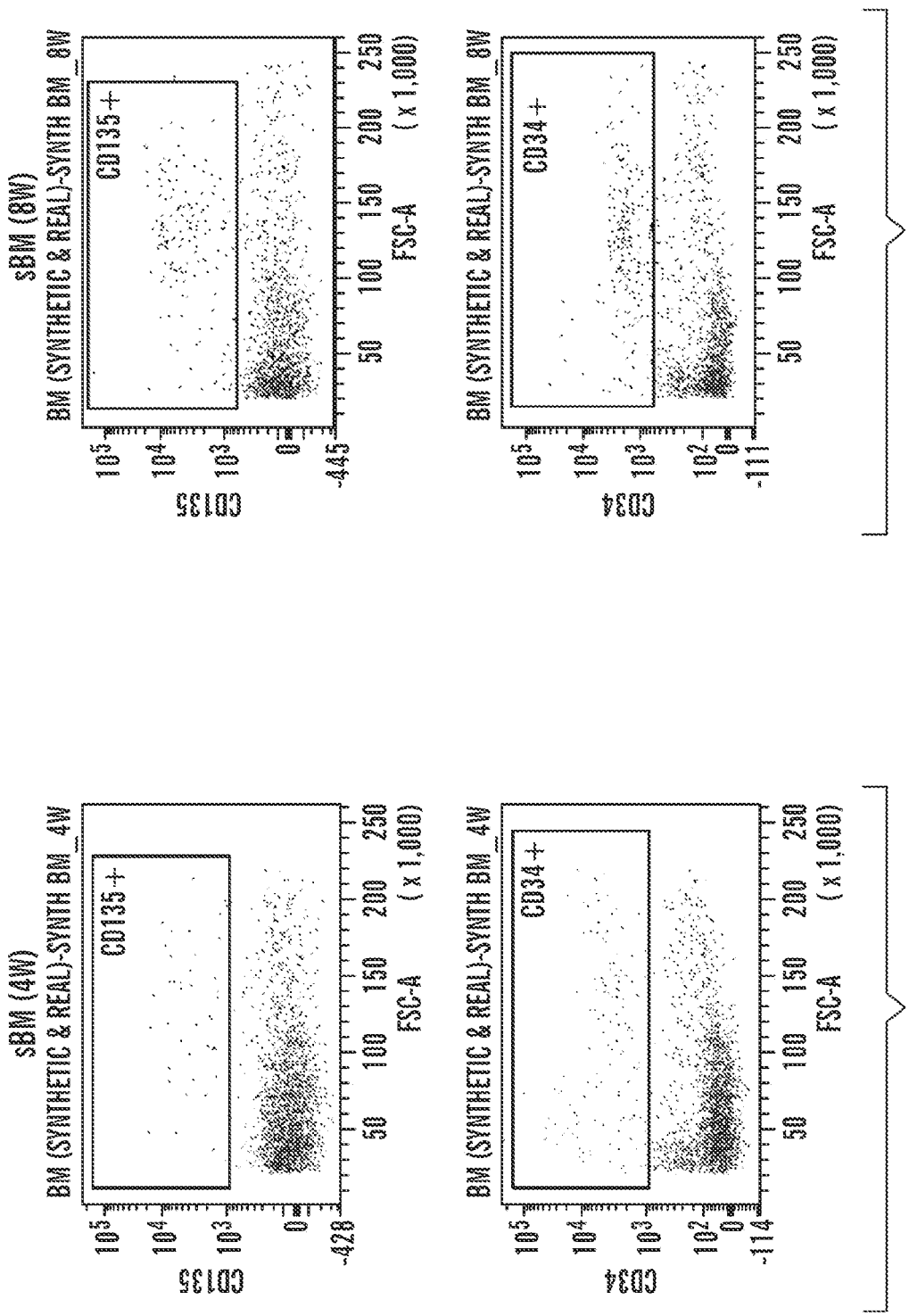

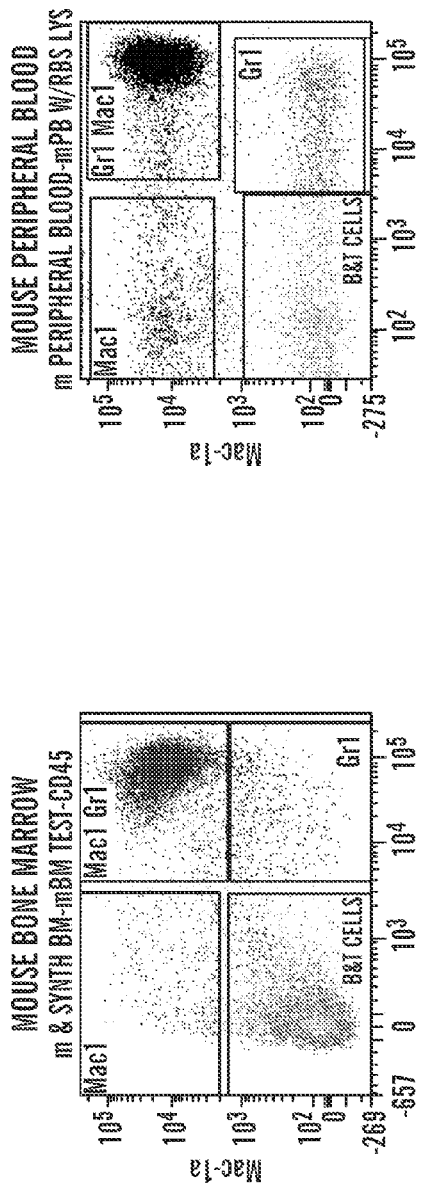
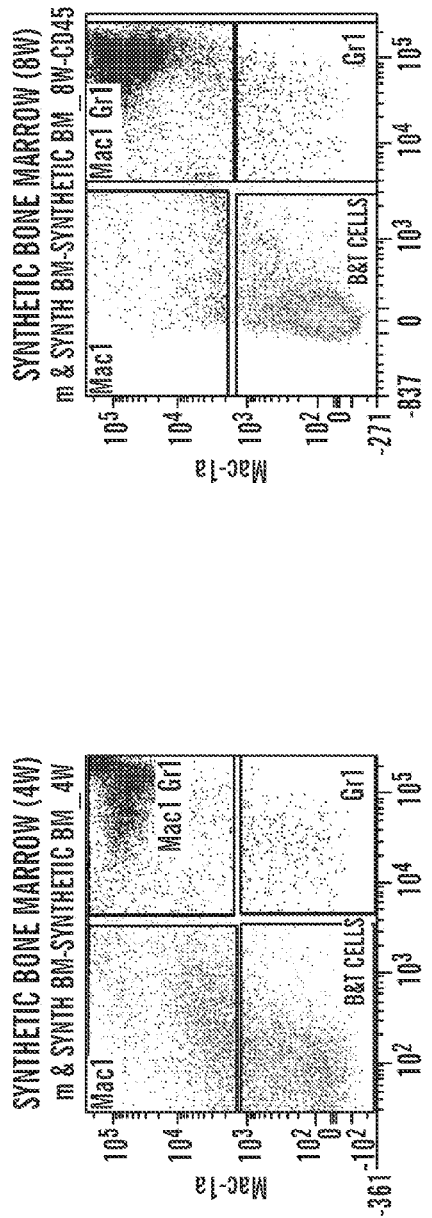
FIG. 12A  FIG. 12B  FIG. 12C  FIG. 12D

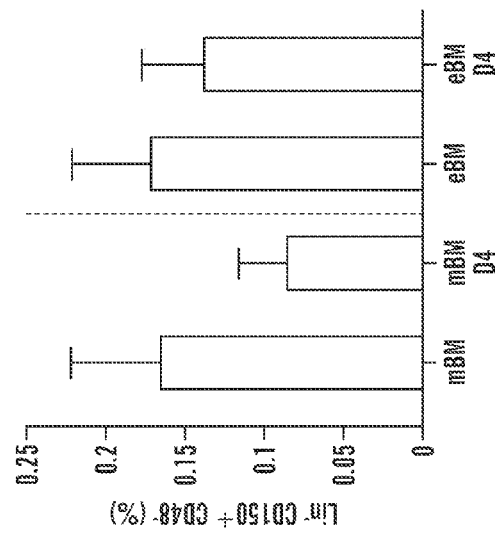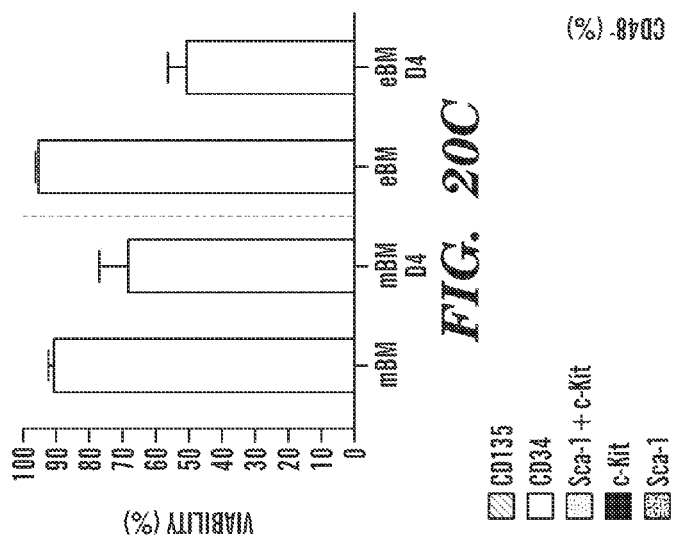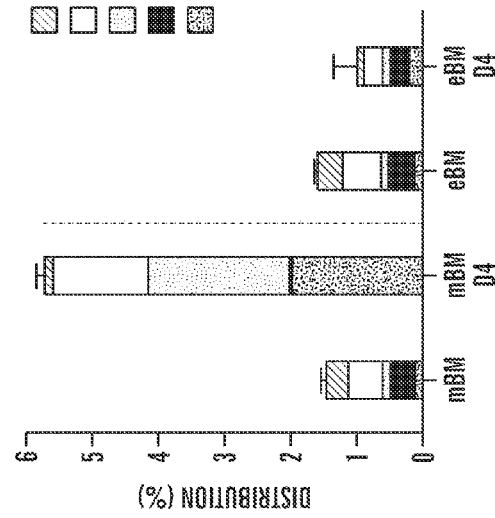

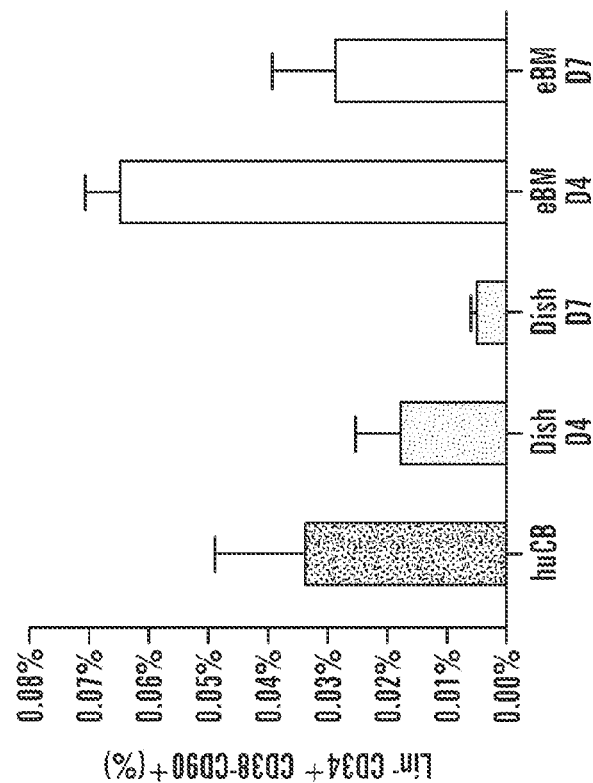
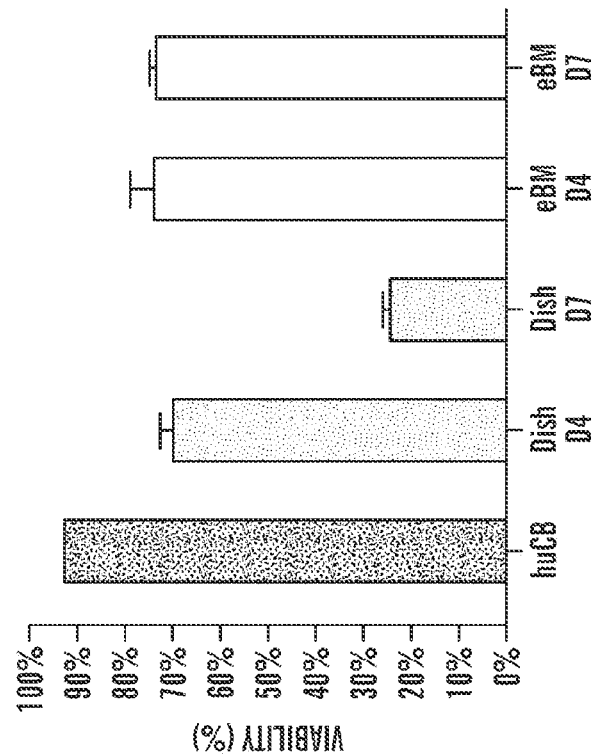
FIG. 21A
FIG. 21B

SEQUENCE LISTING

<160> NUMBER OF SEQ ID NOS: 2

<210> SEQ ID NO 1
<211> LENGTH: 396
<212> TYPE: PRT
<213> ORGANISM: Homo sapiens

<400> SEQUENCE: 1

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365
```

```
Ile Ser Met Leu Tyr Leu Asp Glu Asn Glu Lys Val Leu Lys Asn
    370                 375                 380

Tyr Gln Asp Met Val Val Glu Gly Cys Gly Cys Arg
385                 390                 395

<210> SEQ ID NO 2
<211> LENGTH: 408
<212> TYPE: PRT
<213> ORGANISM: Homo sapiens

<400> SEQUENCE: 2

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350
```

```
Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

METHODS AND USES FOR EX VIVO TISSUE CULTURE SYSTEMS

CROSS REFERENCE TO RELATED APPLICATIONS

This application is a 35 U.S.C. § 371 National Phase Entry Application of International Application No. PCT/US2012/040188 filed May 31, 2012, which designates the U.S., and which claims benefit under 35 U.S.C. § 119(e) of U.S. Provisional Application No. 61/492,609 filed Jun. 2, 2011 and U.S. Provisional Application No. 61/601,745 filed Feb. 22, 2012, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Nov. 13, 2013, is named 002806-069763-US_SL.txt and is 7,311 bytes in size.

TECHNICAL FIELD

The technology described herein relates to methods and uses for ex vivo systems of living organs, tissues, and cells.

BACKGROUND

One limitation of tissue engineering and in vitro tissue growth strategies has been the challenge of recapitulating the natural structures of tissues and organs. In order to grow even the simplest of tissues, an exquisite balance of a complex mixture of growth factors, signaling molecules, nutrients, extracellular matrix scaffolds and mechanical forces that vary over time must be achieved, or cells will fail to organize correctly into tissue and organ structures. Alternatively, removing existing tissue or organ structures from a subject in order to study or propagate the tissue ex vivo can cause damage to the tissues and reestablishing the proper flow of nutrients into the tissue in culture or during transport for transplantation has proven difficult.

For example, hematopoietic stem cells, useful as a source of therapeutic bone marrow material for transplantation or for manufacturing differentiated blood cell replacements (e.g. erthyrocytes, platelets, or leukocytes) have been intractable to in vitro culture. Some investigators have attempted to culture and expand hematopoietic stem cells (HSCs) in vitro, but long-term engraftment and host hematopoietic reconstitution from cultured HSCs has been extremely inefficient (Csaszar, E. et al. Cell Stem Cell 10, 218-229 (2012); Boitano, A. E. et al. Science 329, 1345-348 (2010); Cook, M. M. et al. Tissue Eng. 18, 319-328 (2012)). Multi-potent HSCs are difficult to maintain in vitro because they commonly differentiate when removed from the complex bone marrow niche that contains numerous chemical, structural, mechanical and spatial signals that are required for maintenance of their stem cell features (Takagi, M. J. Biosci. Bioeng. 99, 189-196 (2005); Nichols, J. E. et al. Biomaterials 30, 1071-1079 (2009); Maggio, N. D. et al. Biomaterials 32, 321-329 (2011)).

Thus, there is a need for experimental tools and methods that promote assembly of multi-cellular and multi-tissue organ-like structures that exhibit the key structural organization and physiological function of the tissues and organs being modeled and that can survive and remain functional ex vivo.

SUMMARY

The technology described herein is directed to methods and devices that can be used to induce functional cell, tissue and organ structures to form and/or develop within an implantation device by implanting it in vivo within the body of a living animal, and allowing cells and tissues to impregnate the implantation device and establish normal microenvironmental architecture, tissue-tissue interfaces, and/or organ-like structures and functions. Then the whole device, including the contained cells and tissues, can be surgically removed. In some embodiments, the cell, tissues, and/or organoids that formed and/or developed in the implantation device while it was implanted or afterward, and optionally, the implantation device, can be transplanted into another animal. In some embodiments, the cell, tissues, and/or organoids formed and/or developed in the implantation device while it was implanted or afterward can be maintained as viable in vitro by perfusing the cell, tissues, and/or organoids with media and/or gases necessary for cell survival within the implantation device or after being removed from the implantation device and placed in a microfluidic device. The complex organ mimic can be maintained viable in vitro through, for example, continuous perfusion via microfluidic channels and be used to study highly complex cell and tissue functions in their normal 3D context with a level of complexity not possible using any existing in vitro model system. It can also be used as a manufacturing strategy to produce transplantable therapeutic micro-organs or as a manufacturing device to manufacture cells or cell products.

In accordance with one aspect of the technology described herein, an implantation device having at least one cell growth chamber can be implanted in vivo into an animal. In some embodiments, the implantation device contains compounds which induce the growth of the desired tissue type or types in a chamber that has one or more corresponding cell growth chamber openings (e.g. ports) to the surrounding tissue space. By way of example, in order to induce the growth of bone, the implantation device can contain bone-inducing materials, i.e. demineralized bone powder and/or bone morphogenic proteins (BMPs). As a result of wound healing, connective tissues containing microcapillaries and mesenchymal stem cells can grow into the cell growth chamber of the implantation device and, due to the presence of the bone-inducing material, can form bone with spaces that recruit circulating hematopoietic precursor cells to form fully functional bone marrow. In some embodiments, the implantation device can be implanted subcutaneously. In some embodiments, the implantation device can be implanted under the kidney capsule. In some embodiments, the implantation device can be implanted intraperitoneally. In some embodiments, the implantation device can be implanted intramuscularly. In some embodiments, the implantation device can be implanted subcutaneously with at least one cell growth chamber opening (e.g. port allowing the entry and/or exist of cells) facing the surface of a muscle.

In some embodiments, once the tissue ingrowth process is complete, the surgical site can be reopened, the implantation device with newly formed and/or developed organ-like tissue composites can be dissected from the surface of the surrounding tissues. In some embodiments, the cell, tissue and/or organoid, and optionally, the implantation device can be transplanted into a second animal. In some embodiments, the cell, tissue, and/or formed and/or developed organoid can be removed from the implantation device and placed in a microfluidic device to perfuse the newly formed and/or developed tissues and structures with medium, oxygen, nutrients and supportive factors necessary to maintain its viability and function in vitro. In some embodiments, the cell, tissue, and/or organoid and the implantation device can be removed and coupled to a microfluidic device and/or system to perfuse the newly formed and/or developed tissues and structures with medium, oxygen, nutrients and supportive factors necessary to maintain its viability and function in vitro.

In accordance with one aspect of the technology described herein, the implantation device is a microfluidic device. In some embodiments, a microfluidic device having at least one cell growth chamber and at least one abutting, fluid flow channel, can be implanted in vivo into an animal in which the implantation device contains compounds which induce the growth of the desired tissue type or types in a channel that has one or more corresponding cell growth chamber openings (e.g. ports allowing cells to enter and/or exit the device) to the surrounding tissue space. The cell growth chamber is the portion of the microfluidic device where cells, tissues, and/or organoids will form and/or develop. The fluid flow channel is the portion of the microfluidic device through which fluid will enter, pass through, and/or exit the microfluidic chip. In some embodiments, the cell growth chamber is a portion of one or more fluid flow channels (i.e. the fluid flow channel can comprise the cell growth chamber). In some embodiments, the cell growth chamber is connected to the one or more fluid flow channels, but the fluid flow channels do not comprise the cell growth chamber. The fluid flow channel could be closed during implantation by closing its end ports or filling it with a solid removable material, such as a solid rod or a plug. By way of example, in order to induce the growth of bone, the implantation device can contain bone-inducing materials, i.e. demineralized bone powder and/or bone morphogenic proteins (BMPs). As a result of wound healing, connective tissues containing microcapillaries and mesenchymal stem cells can grow into the cell growth chambers of the implantation device and, due to the presence of the bone-inducing material, can form and/or develop bone with spaces that recruit circulating hematopoietic precursor cells to form fully functional bone marrow. In some embodiments, the microfluidic device can be implanted subcutaneously. In some embodiments, the microfluidic device can be implanted under the kidney capsule. In some embodiments, the microfluidic device can be implanted intraperitoneally. In some embodiments, the microfluidic device can be implanted intramuscularly. In some embodiments, the microfluidic device can be implanted subcutaneously with at least one cell growth chamber opening facing the surface of a muscle.

In some embodiments, once the tissue ingrowth process is complete, the surgical site can be reopened, and the fluid flow channel can be reopened by removing the rod or plugs and can then be connected to a fluid reservoir so that culture medium containing nutrients and gases necessary for cell survival can be pumped through the fluid flow channel and passed through the pores of the separator component (e.g., membrane or micropillars) into the cell growth chamber containing the formed tissue. The entire microfluidic device can then be cut free from the surrounding tissue, and with the medium flowing into the microfluidic device, could be removed from the animal and passed to a tissue culture incubator and maintained in culture with, for example, continuous fluid flow through the second channel, and additional flow can be added to the first channel as well if desired by connecting to their inlet and outlet ports.

The cells, tissue and/or organ structures contained within the implantation device can form and/or develope the correct tissue structure and organization and thus create a complex three-dimensional microenvironment that more closely mimics in vivo conditions than other technologies for culturing cells in vitro.

In some embodiments, the tissue contained in the implantation device could then be used to study intact tissue function in vitro as in a controlled environment. In some embodiments, the tissue contained in the implantation device could then be used to screen compounds for interactions with that tissue, including toxicity, or modulation of development, function, structure, growth, survival and/or differentiation.

In some embodiments, the tissue and/or cells contained in the implantation device could then be used to produce cells or cell-derived factors. In some embodiments, the cells or cell-derived factors thus produced can be administered to a subject. In some embodiments, the tissue contained in the implantation device comprises bone marrow. In some embodiments, the hematopoietic cells or bone marrow-derived factors can be administered to a subject. In some embodiments, the subject can have a cancer, a hematopoietic disease, or a compromised immune system. In some embodiments, the subject can have undergone chemotherapy or radiation therapy.

In some embodiments, the implantation device can be implanted into an animal having human or humanized cells, thereby providing human or humanized tissue and/or cells in the implantation device. In some embodiments, the human cells in the animal can be obtained from a cancer or a human having a disease which affect the cell type growing in the implantation device.

In some embodiments, the implantation device can be implanted into an animal having human or humanized bone marrow and/or hematopoietic cells, thereby providing human or humanized bone marros tissue and/or hematopoietic cells in the implantation device. In some embodiments, the human cells in the animal can be obtained from the bone marrow of a healthy human subject or of a human with a cancer or other disease which affects hematopoietic cells.

In some embodiments, the tissue and/or cells contained in the implantation device or the tissue and/or cells removed from the implantation device could be transplanted to a second subject. In some embodiments, the bone marrow tissue and/or hematopoietic cells contained in the implantation device or the bone marrow tissue and/or hematopoietic cells removed from the implantation device could be transplanted to a second subject. In some embodiments, the subject can have a cancer, a hematopoietic disease, radiation toxicity, or a compromised immune system. In some embodiments, the subject can have undergone chemotherapy or radiation therapy.

In some embodiments, more than one implantation device containing tissue and/or cells or more than one tissue can be implanted into the second subject. By way of non-limiting example, human bone marrow in an implantation device could be implanted into a mouse and human cancer cells could be implanted, either as a biopsy or contained in a second implantation device, at a second site in the same mouse. This model can be used to study human immune response to cancer. A further non-limiting example is the implantation of human bone marrow in a chip and a second human tissue implant, such as skin, at a second site in the subject in order to study autoimmune disease.

In some embodiments, the first subject in which the implantation device is implanted can be a non-human subject having human or humanized cells. In some embodiments, the first subject and the second subject can be the same subject and the method comprises an additional step of maintaining the implantation device containing tissue and/or cells in vitro between removal from the site of implantation and transplantation back into the subject. In some embodiments maintaining can comprise freezing, refrigeration and/or connecting the implantation device to a microfluidic system and providing a perfusion fluid to the implantation device after removing the chip from the site of implantation and before transplanting it back into the subject.

BRIEF DESCRIPTION OF THE DRAWINGS

FIG. 2A shows an optical top view and a diagram of a vertical cross-section of a Single Channel Format device. FIG. 2B shows an optical top view and a diagram of a vertical cross-section of a Closed Channel Format device.

FIG. 3A shows a Well Format implantation device next to a dime for perspective. FIG. 3B shows a Well Format implantation device with two openings and a Well Format implantation device with one opening after in vivo culture. FIG. 3C shows a diagram of a Well Format implantation device with two openings. FIG. 3D shows a diagram of a Well Format implantation device with one opening.

FIGS. 4A-4B depict PDMS wells sutured to muscle in subcutaneous sites in mice. FIG. 4C depicts an optical image of the implant in the PDMS well after 8 weeks of subcutaneous implantation.

FIGS. 6A-6C show H&E stains of the contents of a Well Format implantation device with one opening 8 weeks after implantation. FIG. 6A is oriented such that the opening of the implantation device would be below each image. Scale bars as shown.

FIG. 9E compares the populations on one graph.

FIGS. 10A-10E show the results of FACS analysis to detect hematopoietic progenitor cells. 10A shows the profile obtained from mouse bone marrow (mBM), 10B shows the profile obtained from mouse peripheral blood (mPB) that the red blood cells have been lysed, 10C shows the profile obtained from tissue recovered from the implantation device after 4 weeks of in vivo growth (sBM 4 w) and 10D shows the profile obtained from tissue recovered from the implantation device after 8 weeks of in vivo growth (sBM 8 w). Antibodies were used which recognized the markers indicated on x- and y-axes in FIGS. 10A-10D. FIG. 10E compares the populations on one graph.

FIG. 11E compares the populations on one graph.

FIGS. 12A-12E show the results of FACS analysis to detect leukocytes. 12A shows the profile obtained from mouse bone marrow (mBM), 12B shows the profile obtained from mouse peripheral blood (mPB), 12C shows the profile obtained from tissue recovered from the implantation device after 4 weeks of in vivo growth (sBM 4w), and 12D shows the profile obtained from tissue recovered from the implantation device after 8 weeks of in vivo growth (sBM 8w). Antibodies were used which recognized the markers indicated on x- and y-axes in FIGS. 12A-12D. FIG. 12E compares the populations on one graph.

FIG. 14A is a diagram of the microfluidic device and FIG. 14B is an optical image of the microfluidic device with a biopsy sample present in the cell growth chamber.

FIG. 16B depicts high magnification micrographs of natural mouse bone marrow from a femur and the synthetic bone marrow from the implantation device of FIG. 16A. FIGS. 16C-16D depict graphical representations of hematopoietic stem and progenitor populations (FIG. 16C) and differentiated blood cell populations (FIG. 16D) present in a mouse femur (mBM), the engineered bone marrow 4 weeks (eBM 4 wk), and 8 weeks (eBM 8 wk) after being implanted into a mouse, compared to mouse peripheral blood (mPB).

(FIG. 19D) Comparison of a cross-section of the engineered bone marrow 8 weeks following implantation with a cross-section of the mouse vertebra. The micro-CT images demonstrate the structure and extent of bone mineralization.

FIGS. 20A-20E depict the outcomes of a transplant experiment. FIG. 20A depicts the extent of engraftment of lethally irradiated mice transplanted with mouse femur bone marrow cells or engineered bone marrow cells following 4 days of in vitro culture. Engraftment was assessed 6 and 16 weeks post transplantation. FIG. 20B depicts the distribution of differentiated blood cells within the engrafted CD45+ population. (FIG. 20C) Viability of blood cells following 4 days of culture, compared to freshly isolated mouse femur bone marrow (mBM) and engineered bone marrow (eBM). The engineered bone marrow was cultured in the device for 4 days (eBM, D4). Bone marrow cells isolated from a mouse femur were cultured on a stromal cell layer in a dish for 4 days (mBM, D4). (FIGS. 20D-20E) Graphical representation of hematopoietic stem and progenitor populations (FIG. 20D) and a long-term hematopoietic stem cell population (Lin-CD150+CD48-) (FIG. 20E).

FIGS. 21A-21B depict graphs of the results of human cord blood cell culture. The engineered bone marrow containing hCB cells was cultured in the microfluidic device for 4 days (eBM, D4) or 7 days (eBM, D7) while perfusing culture media to maintain HSCs. hCB cells were also cultured in a dish for 4 days (mBM, D4) or 7 days (mBM, D7). (FIG. 21A) Viability of hCBs following 4 days of culture, compared to freshly isolated hCB. (FIG. 21B) Graphical representation of hematopoietic stem cell population (Lin-CD34+CD38-CD90+).

DETAILED DESCRIPTION

Definitions

Figure 1A:
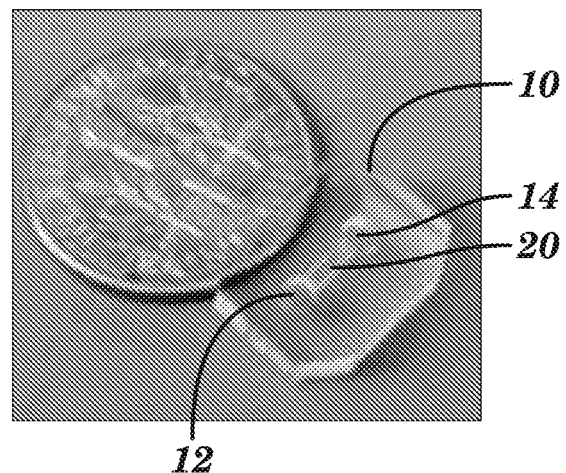
FIGS. 1A-1C show diagrams and a photograph of one embodiment (the Open Channel Format) of the microfluidic device described herein.

For convenience, the meaning of some terms and phrases used in the specification, examples, and appended claims, are provided below. If there is an apparent discrepancy between the usage of a term in the art and its definition provided herein, the definition provided within the specification shall prevail.

Definitions of common terms in cell biology and molecular biology can be found in "The Merck Manual of Diagnosis and Therapy", 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology are also be found in Benjamin Lewin, Genes IX, published by Jones & Bartlett Publishing, 2007 (ISBN-13: 9780763740634); Kendrew et al. (eds.), Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the experiments, assays, and methods described herein were performed using standard procedures, as described, for example in Methods in Enzymology, Volume 289: Solid-Phase Peptide Synthesis, J. N. Abelson, M. I. Simon, G. B. Fields (Editors), Academic Press; 1st edition (1997) (ISBN-13: 978-0121821906); U.S. Pat. Nos. 4,965,343, and 5,849,954; Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference sample), or any decrease between 10-100% as compared to a reference level. In the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Subject includes any subset of the foregoing, e.g., all of the above, but excluding one or more groups or species such as humans, primates or rodents. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of bone and/or bone marrow formation and growth. A subject can be male or female.

As used herein, "hematopoietic disease," "hematopoietic condition" or "hematopoietic disorder" are used interchangeably and refer to a condition in which any cell type of the hematopoietic lineage is overproduced, underproduced, or displays aberrant function or behavior.

As used herein, a "hematopoietic stem cell" refers to a cell capable of self-renewal and differentiating to become one of the mature cell types of the hematopoietic cell lineage.

As used herein, a "hematopoietic progenitor cell" refers to a cell capable of differentiating to become at least one of the mature cell types of the hematopoietic cell lineage. Hematopoietic progenitor cells include, but are not limited to, pre-T cells, pre-B cells, blast colony-forming cells, megakaryocyte erythrocyte progenitor (MEP), common multipotent progenitor (CMP), granulocyte/macrophage progenitor (GMP), and granulocyte-macrophage colony-stimulating factor cells.

As used herein, a "hematopoietic cell" includes any mature cell of the hematopoietic lineage, any hematopoietic progenitor cell, and/or any hematopoietic stem cell.

As used herein, "maintain" refers to continuing the viability of a tissue or population of cells. A maintained tissue will have a population of metabolically active cells. The number of these cells can be roughly stable over a period of at least two weeks or can grow.

As used herein, the term "implantation device" or "chip" refers to a structure or substrate which contains therein or thereon at least a cell growth chamber and one port. The implantation device can be implanted in a subject and be colonized by cells, tissues, and/or organoids as described herein. In some embodiments, an implantation device can refer to a microfluidic device, microfluidic chip, or a portion thereof. In some embodiments, the implantation device can be coupled to one or more additional structures to create a microfluidic device or chip.

As used herein, the terms "microfluidic device" and "microfluidic chip" are used interchangeably and refer to a structure or substrate having microfluidic structures contained therein or thereon. In some embodiments, the chip can be detachably connected to a microfluidic system.

As used herein, the term "channel" refers to any capillary, channel, tube, or groove that is deposed within or upon a substrate. A channel can be a microchanel; a channel that is sized for passing through microvolumes of liquid.

As used herein, the term "cell growth chamber" refers to a void within an implantation device that can be shaped to control the growth of ingrowth cells, tissues, and/or organoids so that the cells, tissues and/or organoids take on a specified 3D form. In some embodiments, cells, tissues, and/or organoids are placed in a cell growth chamber. In some embodiments, cells, tissues, and/or organoids are induced to colonize a cell growth chamber. In some embodiments a cell growth chamber can be a channel.

As used herein, the term "port" refers to a portion of the implantation device or microfluidic chip which provides a means for fluid and/or cells to enter and/or exit the device and/or chip. A port can allow passage of fluid and/or cells into and/or out of the device and/or chip during in vivo growth. The port can be of a size and shape to accept and/or secure a connection with tubes, connections, or adaptors of a microfluidic system and allow passage of fluid and/or cells when attached to a microfluidic system. A port can be configured to allow entry of only fluid or only cells into and/or out of the device or can be configured to allow entry of either fluid and/or cells into and/or out of the device. A port that provides a means for cells to enter and/or exit the cell growth chamber from the exterior of the device and/or chip is also referred to herein as a "cell growth chamber opening."

As used herein, the term "microfluidic system" refers to a machine capable of the manipulation of microliter and/or nanoliter volumes of fluids.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

All patents and other publications identified are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Implantable Devices

Figure 1B:
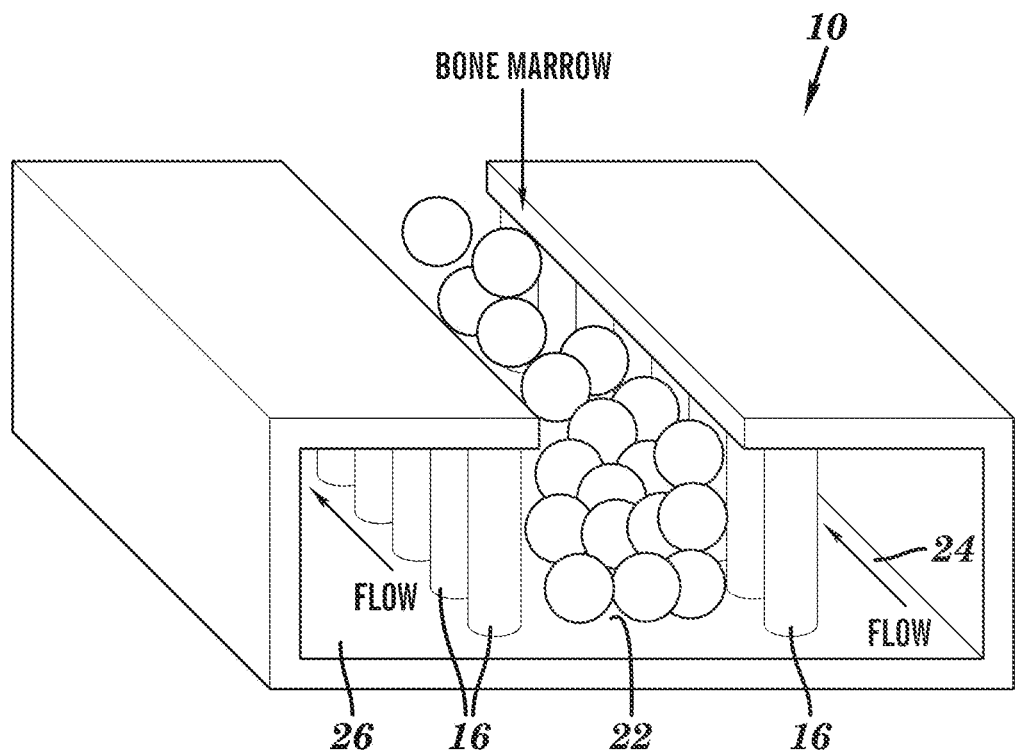
Figure 1C:
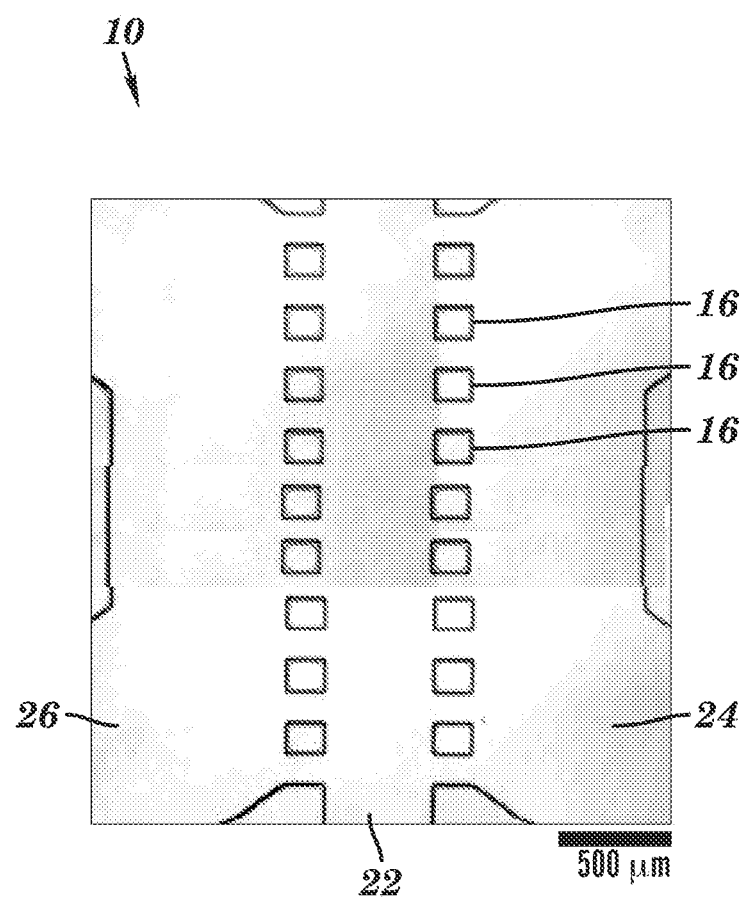

FIGS. 1A-1C depict one embodiment of the implantation device, or chip, described herein. The embodiments shown in FIGS. 1A-1C shall be referred to herein as the Open Channel Format. FIG. 1A shows a PDMS chip 10 next to a dime for perspective, although the implantation device can be larger or smaller according to the application of the implantation device. As shown, the chip can be formed in an octagonal shape, although other shapes can be used. In some embodiments of the technology described herein, the size and shape of the chip 10 can be selected to enable the chip to be used in a particular microfluidic system. In some embodiments, the size, shape and configuration of the chip 10 can be selected so that the chip can be used as a replacement for to other chips provided by manufacturers or suppliers for a particular microfluidic system. In some embodiments, the chip 10 can include one or more inlet ports 12 connected to one or more outlet ports 14 by one or more microfluidic channels 20. The ports 12, 14 can be provided in the appropriate size and shape necessary to accept the tubes and/or connectors of a particular microfluidic system. In some embodiments, the inlet port(s) 12 and the outlet port(s) 14 can be connected to enable fluid entering the inlet port(s) 12 to pass through some or all of the fluid channel(s) 20 before reaching the outlet port(s). In some embodiments, multiple ports can be connected to a fluid channel.

FIG. 1B shows a top view of one embodiment of the technology described herein. In accordance with some embodiments of the technology described herein, the chip 10 can include one or more fluid channels 24, 26 and one or more cell growth chamber(s) 22. In accordance with one embodiment of the technology described herein, each channel 22, 24, 26 can be at least 100 μm in width, at least 200 μm in width, at least 300 μm in width, at least 500 μm in width, at least 750 μm in width, at least 1000 μm in width, or at least 2000 μm in width. In accordance with one embodiment of the technology described herein, two fluid channels 24, 26 can be separated by a cell growth chamber 22. The boundary between the cell growth chamber and a fluid channel can be created by micropillars 16. In this embodiment, the gaps between the micropillars 16 can be adjusted to provide a predefined amount of fluid exchange between the fluid channel(s) 24, 26 and the cell growth chamber 22 to sustain and promote cell growth. A micropillar can be, for example, at least 25 μm in width, at least 50 μm in width, at least 100 μm in width, at least 250 μm in width, at least 500 μm in width, or at least 1000 μm in width. The gaps between the micropillars can be roughly the same size as the micropillars. The gaps between the micropillars can be, for example, at least 25 μm in width, at least 50 μm in width, at least 100 μm in width, at least 250 μm in width, at least 500 μm in width, or at least 1000 μm in width.

FIG. 1C shows a cross-section of the fluid channels 24, 26 and cell growth chamber 22 in a microfluidic device according to an embodiment of the technology described herein. In accordance with some embodiments of the technology described herein, there can be one fluid channel abutting the cell growth chamber. In alternative embodiments, there can be two, three, four, five, six, or more fluid channels abutting the cell growth chamber. The fluid channels can extend parallel to the cell growth chamber 22 and positioned along side as well as above and/or below the cell growth chamber 22. In some embodiments, different fluid channels can abut the cell growth chamber at different locations along the cell growth chamber. In some embodiments, the cell growth chamber is abutted by fluid channels on approximately 180 degrees total. In some embodiments, the cell growth chamber is abutted by fluid channels on approximately 45 degrees, approximately 90 degrees, approximately 135 degrees, approximately 180 degrees, approximately 225 degrees, approximately 270 degrees, or approximately 315 degrees. In some embodiments the fluid channels and/or cell growth chamber have a square cross-section. In other embodiments, the fluid channels and/or cell growth chamber can each have an approximately circular cross-section, a partly circular cross-section, an ovoid cross-section, a rectangular, a pentagonal, a hexagonal, a septagonal, an octagonal, a nonagonal, or a decagonal cross-section. In some embodiments, as shown in FIG. 1C, at least one side of the cell growth chamber (6) is not bounded by any other component of the PDMS chip (1) and is able to be directly exposed to the environment surrounding the chip.

In accordance with some embodiments, each channel 22, 24, 26 can be at least 500 μm in height, at least 200 μm in height, at least 300 μm in height, at least 500 μm in height, at least 750 μm in height, at least 1000 μm in height, or at least 2000 μm in height. The depth of the cell growth chamber can be at least 50 μm in height, at least 200 μm in height, at least 300 μm in height, at least 500 μm in height, at least 750 μm in height, at least 1000 μm in height, or at least 2000 μm in height. The thickness, i.e. the height dimension of the chip or carrying microfluidic device can be sufficient to provide structural integrity to the implantation device for its intended use and purpose. In some embodiments, the microfluidic device can range in thickness from at least 250 μm in height, at least 500 μm in height, at least 1 mm in height, at least 2 mm in height, at least 5 mm in height, or at least 10 mm in height.

In the embodiment shown in FIGS. 1A-1C, the chip is 500 μm in depth. The fluid channels 24, 26 are 750 μm-1 mm in width. The cell growth chamber 22 is 3 mm long, 500 μm in width and 250 μm in depth. The posts 16 are 100 μm×200 μm with 100 μm gaps between the posts.

Figure 2B:
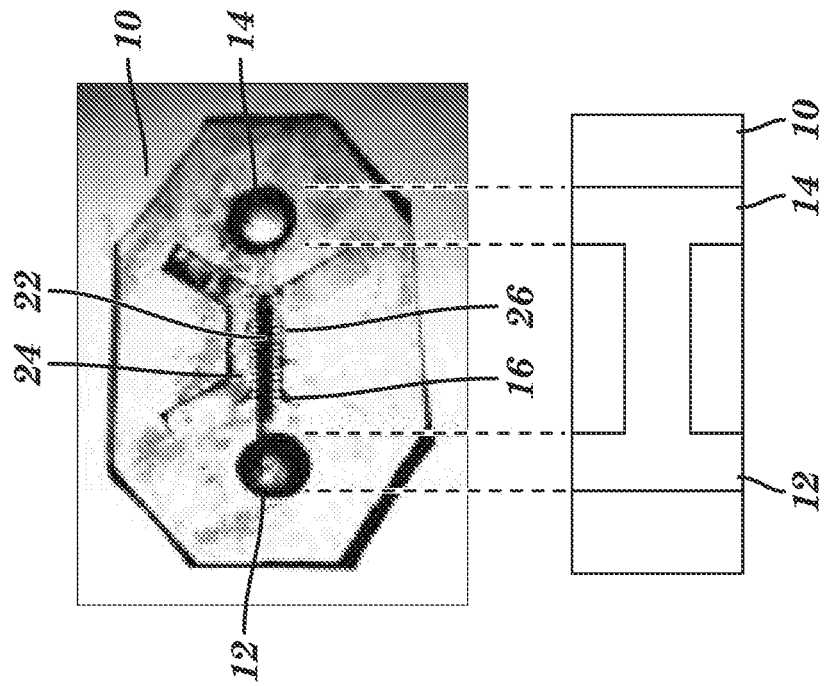
FIGS. 2A-2B show two embodiments of the microfluidic device described herein.
Figure 2A:
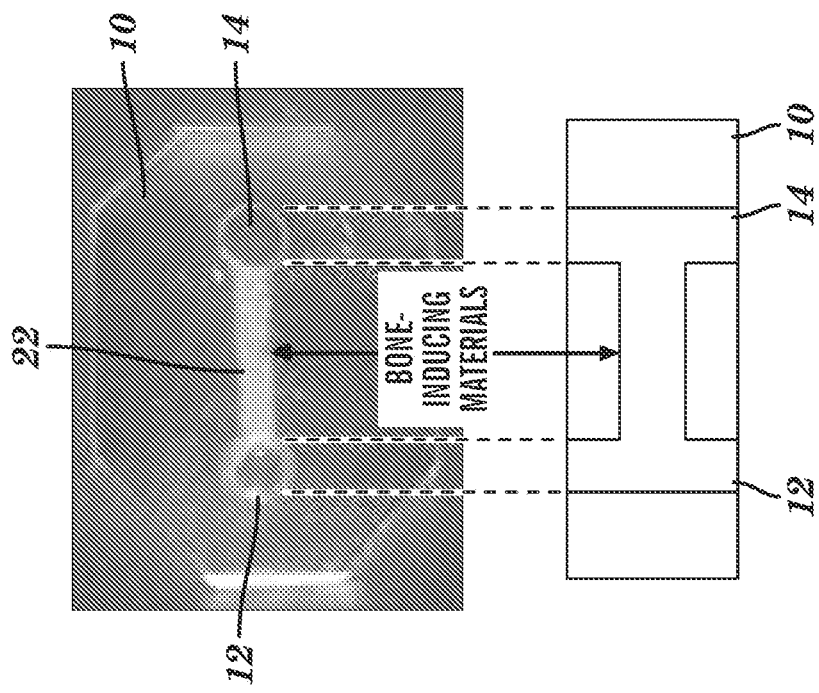

FIGS. 2A-2B and FIGS. 3A-3D show other embodiments of an implantation device according to the technology described herein. FIG. 2A depicts a top view and a horizontal cross-section of the Single Closed Channel Format microfluidic device. In this embodiment, the chip 10 can have 4 ports 12, 14; two being located through the top surface of the chip and two being located through the bottom surface of the chip. The ports can connect to one or more channels (¾), which serves as both a cell growth chamber and a fluid channel.

FIG. 2B depicts a top view and a horizontal cross-section of the Closed Channel Format microfluidic device in accordance with an alternative embodiment. In this embodiment, the chip 10 can include 4 ports 12, 14; two being located on the top surface of the chip and two being located on the bottom surface of the chip. The ports connect to a cell growth chamber 22 flanked by two fluid channels 24, 26. In this embodiment, micropillars 16 can be used to separate the cell growth chamber 22 from the fluid channels 24, 26 but enable transfer of fluids, agents and factors between the fluid channels and the growth channel. In other embodiments, different separation elements can be used including walls with windows, holes or slots, membranes, and other permeable materials.

In the embodiment shown in FIG. 2A, the chip 10 is 8-10 mm in width, 10-15 mm in length and 2 mm in height. The ports 12, 14 are 2 mm in diameter. The cell growth chamber 22 is 3-5 mm long, 1 mm in width, and 400 μm in depth. In the embodiment shown in FIG. 2B, the chip 10 is 8 mm wide and 12 mm in length. The ports 12, 14 are 2 mm in diameter. The cell growth chamber 22 is 3 mm long. The fluid channels 24, 26 are 750 μm-1 mm in width. The posts 16, are 150 μm×200 μm, with 100 μm gaps between the posts.

Figure 3B:
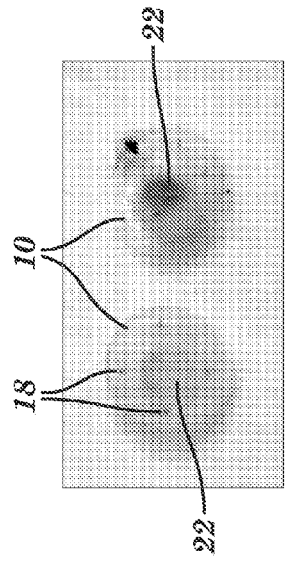
FIGS. 3A-3D show two embodiments of the implantation device described herein.
Figure 3A:
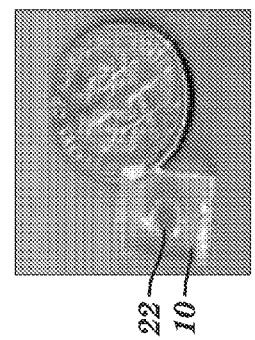
Figure 3D:
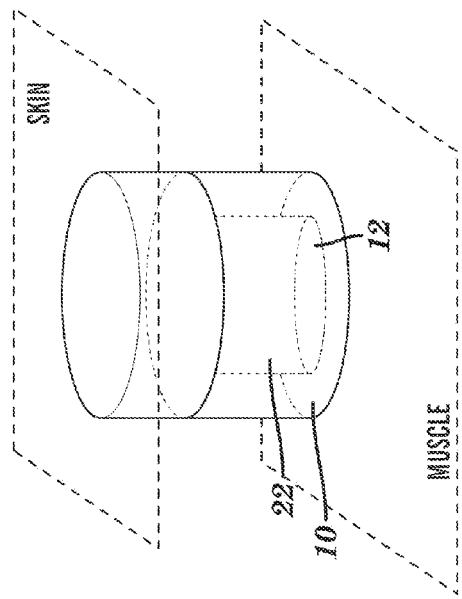
Figure 3C:
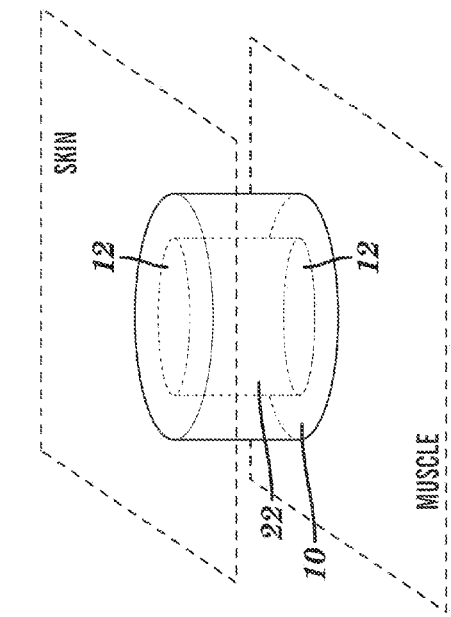

FIGS. 3A-3D depict two Well Format or cartridge embodiments. FIG. 3A shows a photograph of a Well Format chip next to a dime for perspective, although the implantation device can be larger or smaller according to the application of the implantation device. FIG. 3B shows two Well Format chips after the in vivo implantation phase. The implantation device can include holes 18 for suture attachment. FIG. 3C shows a diagram of a Well Format chip having a cell growth chamber 22 connected to two openings (or ports), one through the top of the implantation device and another through the bottom of the implantation device. In this embodiment, the ports 12 (which can, in this embodiment, function as cell growth chamber openings) and cell growth chamber 22 can be coextensive and the fluid channel (not shown) and cell growth chamber 22 can be combined, for example, where the fluid channel extends into or through the cell growth chamber. FIG. 3D shows an embodiment of a Well Format chip 10 having one opening. In this embodiment, the port 12 and cell growth chamber opening can be, at least in part, coextensive. In the embodiments depicted the cell growth chamber 22 is 4 mm in diameter with a depth ranging from 1 mm to 2 mm, the chip 10 is 2 mm in depth and 8 mm in diameter. The holes 18, can be, for example 1 mm in diameter.

The embodiments shown in FIGS. 3A-3D can be part of a cartridge based system. In these embodiments, the chip or device 10 can be, for example, round or circular, as shown in FIGS. 3B-3D or any other polygonal shape, such as a square or rectangle as shown in FIG. 3A. In addition, the cell growth chamber or channel 22 can be, for example, round as shown in FIGS. 3A-3D or any other shape, including oval, square, rectangular, or other polygonal shape. In this embodiment, the chip or device can service as cartridge that is adapted to be inserted into a microfluidic device having one or more fluid channels that enable fluid to flow adjacent the cell growth chamber. In some embodiments, several cartridges 10 can be inserted into a single device.

Figure 13:
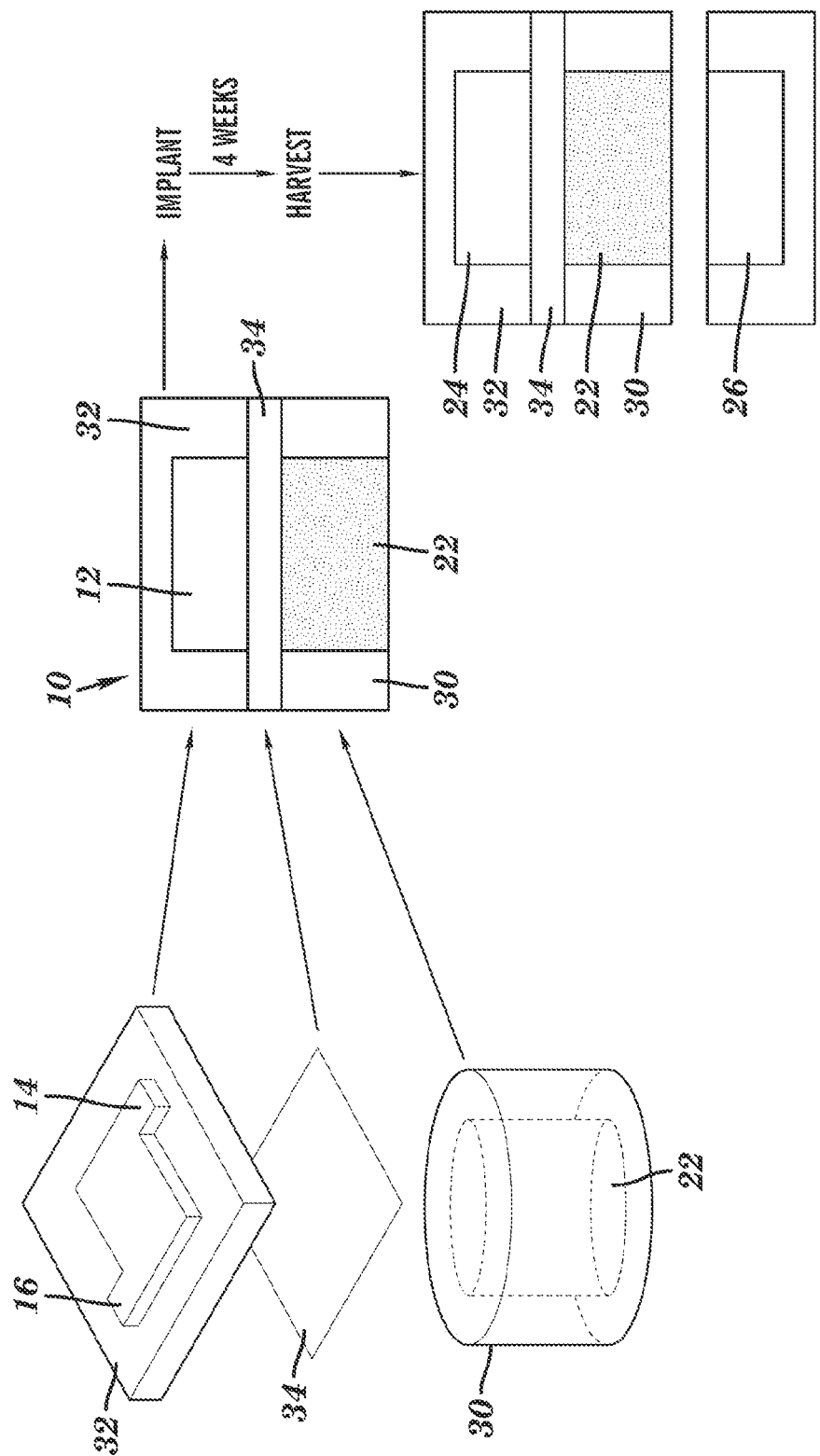
FIG. 13 shows diagrams of a further embodiment of the implantation device having multiple layers which can be separated by a porous membrane.

A further embodiment is shown in FIG. 13. In this embodiment, the chip 10 consists of two PDMS layers 30, 32 separated by a PDMS porous membrane 34. The upper layer 32 has a microfluidic channel 24 to allow medium perfusion, whereas the lower layer has a cylindrical cell growth chamber 22. The implantation device filled with bone-inducing material can be implanted subcutaneously in a subject, and then surgically removed after in vivo growth. Prior to connecting to a microfluidic system, a bottom fluid channel 26 can be bound to the bottom of the implantation device to perfuse culture medium. In the embodiment depicted, the chip 10 ranges from 10-15 mm in length and 8-10 mm in width. The ports 12, 14 are 1 mm in diameter where they connect to the microfluidic system. The bottom layer 30 is 500 µm in depth with a 3 mm diameter cell growth chamber 22. The top layer 32 is 10-15 mm in both width and length with a depth of 1 mm. The fluid channel 24 is 200 µm in depth and 3 mm wide. The ports 14, 16 are 1 mm in width and can range in length from 1 mm to 7 mm. The aspect containing the bottom fluid channel 26 can be identical to the upper layer 32. The PDMS membrane 34 is 10 µm in depth.

Figure 18:
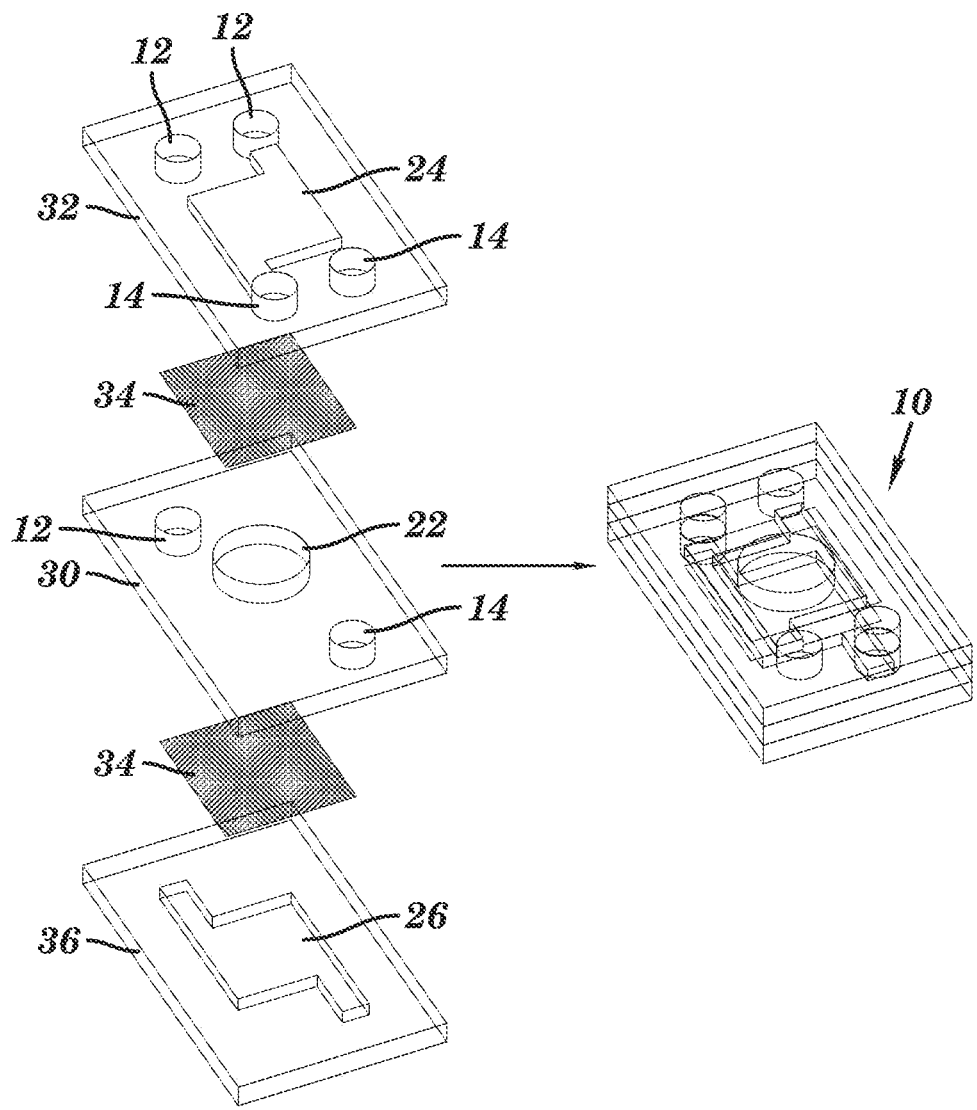
FIG. 18 depicts a further embodiment of the implantation device.
Figure 19B:
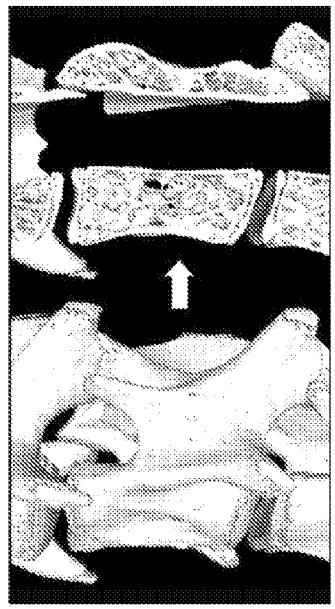
FIGS. 19A-19D depict micro computed tomography (micro-CT) images of engineered bone marrow 4 (FIG. 19A) and 8 weeks (FIG. 19B) following implantation and a mouse vertebra (FIG. 19C).
Figure 19D:
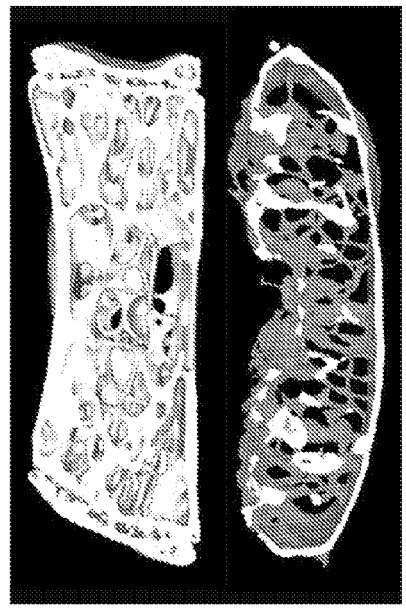
Figure 19A:
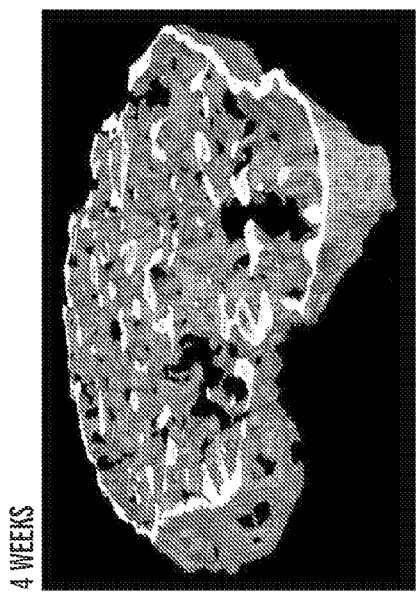
Figure 19C:

A further embodiment is shown in FIG. 18. In this embodiment, the chip 10 comprises a middle PDMS layer 30 comprising a Well Format chip with a cell growth chamber 22 as described above herein. The cell growth chamber 22 in the middle layer 30, filled with bone-inducing material, can be implanted subcutaneously in a subject and then surgically removed after in vivo growth. After removal, each opening of the cell growth chamber 22 of the middle layer 30 can be covered with a PDMS porous membrane 34. The PDMS membranes 34 can then be covered with an upper PDMS layer 32 and a bottom PDMS layer 36. The upper layer 32 has can include a microfluidic channel 24 to allow medium perfusion and ports 12, 14 to connect to a microfluidic system. At least two of the ports connect to the top microfluidic channel 24 and at least two of the ports connect to a bottom microfluidic channel 26 in the bottom layer 36. With the bottom layer 36 and upper layer 32 are in place, the entire chip 10 can be connected to a microfluidic system. In the embodiment depicted, the chip 10 can range from 10-15 mm in length and 8-12 mm in width. The ports 12, 14 can be 0.25 to 3 mm, preferably 1 mm, in diameter where they connect to the microfluidic system, e.g., the ports 12, 14 can be 0.5 to 2 mm in diameter, 0.75 to 2 mm in diameter, or 0.8 to 1.5 mm in diameter where they connect to the microfluidic system. The middle layer 30 can be 400 to 600 µm in depth, e.g. 450 to 550 µm in depth or 475 to 525 µm in depth and can have a 2 to 6 mm diameter cell growth chamber 22, e.g. a 2.5 to 5.5 mm diameter cell growth chamber, a 3 to 5 mm diameter cell growth chamber, or an about 4 mm diameter cell growth chamber. The top layer 32 can be 8-16 mm in both width and length, e.g. 9 to 15 mm, or 10 to 14 mm, or 11 to 13 mm in both width and length and can range from 3 to 7 mm in depth, e.g. from 4 to 6 mm or about 5 mm in depth. The fluid channel 24 can range from 50 to 400 µm in depth, e.g. from 100 to 300 µm, or from 150 to 250 µm or about 200 µm in depth and range from 2 to 6 mm in width, e.g. from 3 to 5 mm, or from 3.5 to 4.5 mm or about 4 mm in width. The ports 12, 14 can be 0.25 to 3 mm, preferably 1 mm, in diameter, e.g., the ports 12, 14 can be 0.5 to 2 mm in diameter, 0.75 to 2 mm in diameter, or 0.8 to 1.5 mm in diameter. The bottom layer 36 containing the bottom fluid channel 26 can have identical dimensions as the upper layer 32. The PDMS membrane 34 can be from 2 to 20 µm in depth, e.g. 5 to 15 µm, 8 to 13 µm, 9 to 11 µm or about 10 µm in depth.

Figure 14B:
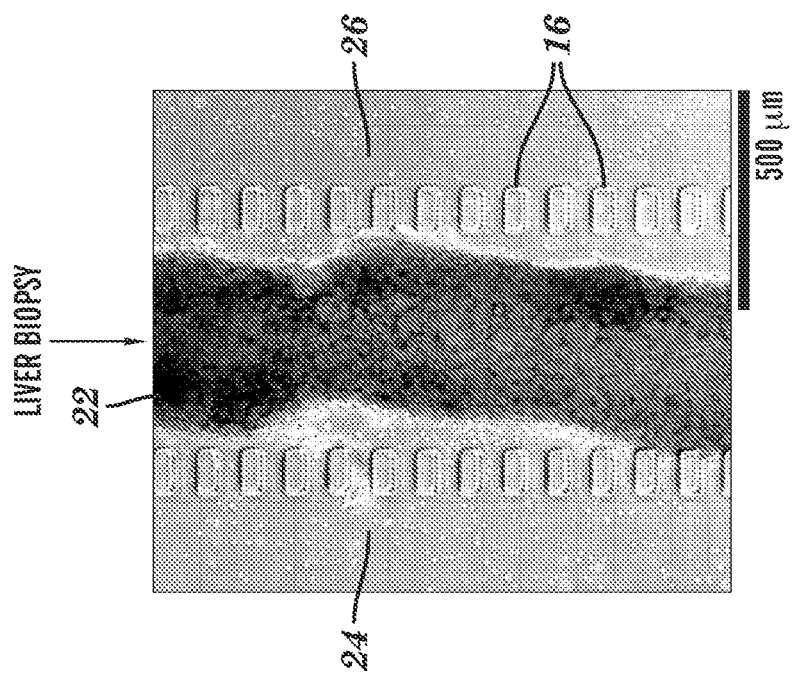
FIGS. 14A-14B show a Biopsy Format device.
Figure 14A:
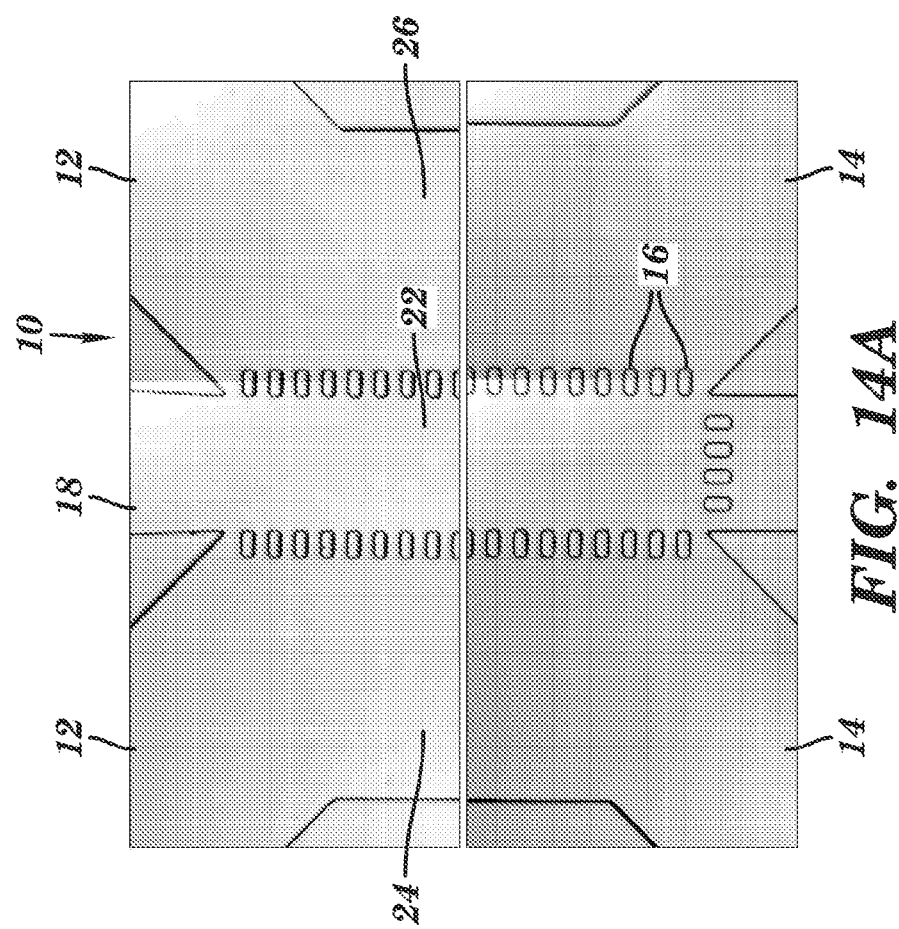

A further embodiment is shown in FIGS. 14A-14B. In this embodiment, the chip 10 (3 mm depth, 50 mm in length) can include 5 ports 12, 14, 18. Four ports 12, 14 connect to the two fluid channels 24, 26. The fifth port 18, a biopsy entry port, connects to the cell growth chamber 22 which is 500 µm in width, 10 mm in length, and range from 200-350 µm in depth. In this embodiment, micropillars 16 (ranging in size from 50-150 µm×100-200 µm, with a 50-100 µm gap between micropillars) can be used to separate the cell growth chamber 22 from the fluid channels 24, 26 (1 mm width) but enable transfer of fluids, agents and factors between the fluid channels and the growth channel. A 500 µm diameter biopsy can be introduced into the middle channel while maintaining negative pressure on the outflow openings.

As a complete system, the chip 10 described herein allows, for example, bone marrow to be cultured in vitro while maintaining bone marrow structure and viability either for extended culture, during transport for transplantation into a subject or transport to a microfluidic system.

The cell growth chamber of the implantation device described herein provides a space which can be colonized by, for example, bone marrow cells or bone marrow precursor cells during in vivo implantation of the implantation device. The open side of the cell growth chamber can allow for migration of cells into the cell growth chamber. When the implantation device is removed from the subject, the chip can be placed into or connected to a compatible microfluidic supply system and a flow of desired fluid can be established by connecting the microfluidic supply system to the inlet and outlet ports (see FIG. 13). The provided fluid flows through the fluid channels and the micropillars or other separation component enables fluid exchange to occur between the cell growth chamber and the fluid channels. In this way, nutrients, growth factors, hormones, test compounds, small molecules, etc can be provided to the cells in the cell growth chamber in order to maintain their viability and/or support their in vitro growth and enable testing and evaluation. Additionally, products and/or waste materials of the cells can be removed from the cell growth chamber and exit into the microfluidic system where they can be disposed of and/or analyzed. The fluid channels also provide a means of delivering test compounds to the bone marrow cells in the cell growth chamber. The bone marrow cells in the cell growth chamber may also give rise to cells which will enter the fluid channels and can be collected by the microfluidic system for subsequent analysis. In accordance with the various embodiments, a porous separation component can be used to separate the cell growth chamber or channel from the fluid channel(s) be chosen to selectively allow fluids, molecules and cells to flow between the cell growth chamber or area and the fluid channel(s). For example, in some embodiments, the micropillars and the gaps between them can be selected to allow at least some of the cells in the cell growth chamber to remain in place and not be removed from the chip by the fluid flow. The size of the pillars and gaps selected can be used to determine the extent of the fluid and material exchange which the cells in the cell growth chamber are subjected to and can be varied to achieve the degree of fluid exchange which is desired and/or necessary for a particular application. In some embodiments the gaps can be made adjustable, for example, using a set of sliding windows (gap) or membrane having adjustable permeability.

The body of the chip or device 10 can be made of a flexible material or a non-flexible material according to the design and application requirements. It should be noted that the microchannel design is exemplary and not limited to the configuration shown in the figures. The chip 10 can be made of a flexible biocompatible material, including but not limited to, a biocompatible material such as polydimethyl siloxane (PDMS), polyurethane or polyimide. The chip 10 can also be made of non-flexible materials like glass, silicon, polysulfone, hard plastic, and the like, as well as combinations of these materials. The chip 10 can also be fabricated using any suitable biocompatible and/or biodegradable materials, such as poly-lactide-co-glycolide acid (PLGA) and in some embodiments, the organ mimic device can be used for transplantation or implantation in vivo.

In accordance with the some embodiments of the technology described herein, the cell growth chamber can be separated from the fluid channel by a separation component (for example, a plurality of micropillars) that can be formed, such as by etching, 3-D printing or micro-machining. Alternatively, the separation component can include a selectively permeable or semi-permeable membrane, for example, also formed from PDMS or porous polycarbonate filter. In other embodiments, the membrane can be made of from other materials or a combination of materials including PDMS.

A biocompatible polymer refers to materials which do not have toxic or injurious effects on biological functions. Biocompatible polymers include natural or synthetic polymers. Examples of biocompatible polymers include, but are not limited to, collagen, poly(alpha esters) such as poly (lactate acid), poly(glycolic acid), polyorthoesters and polyanhydrides and their copolymers, polyglycolic acid and polyglactin, cellulose ether, cellulose, cellulosic ester, fluorinated polyethylene, phenolic, poly-4-methylpentene, poly-acrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, polyglactin, or copolymers or physical blends of these materials.

A biocompatible material can also be, for example, ceramic coatings on a metallic substrate. But any type of coating material and the coating can be made of different types of materials: metals, ceramics, polymers, hydrogels or a combination of any of these materials. Biocompatible materials include, but are not limited to an oxide, a phosphate, a carbonate, a nitride or a carbonitride. Among the oxide the following ones are preferred: tantalum oxide, aluminum oxide, iridium oxide, zirconium oxide or titanium oxide. Substrates are made of materials such as metals, ceramics, polymers or a combination of any of these. Metals such as stainless steel, Nitinol, titanium, titanium alloys, or aluminum and ceramics such as zirconia, alumina, or calcium phosphate are of particular interest.

The biocompatible material can also be biodegradable in that it will dissolve over time and may be replaced by the living tissue. Such biodegradable materials include, but are not limited to, poly(lactic acid-co-glycolic acid), polylactic acid, polyglycolic acid (PGA), collagen or other ECM molecules, other connective tissue proteins, magnesium alloys, polycaprolactone, hyaluric acid, adhesive proteins, biodegradable polymers, synthetic, biocompatible and biodegradable material, such as biopolymers, bioglasses, bioceramics, calcium sulfate, calcium phosphate such as, for example, monocalcium phosphate monohydrate, monocalcium phosphate anhydrous, dicalcium phosphate dihydrate, dicalcium phosphate anhydrous, tetracalcium phosphate, calcium orthophosphate phosphate, calcium pyrophosphate, alpha-tricalcium phosphate, beta-tricalcium phosphate, apatite such as hydroxyapatite, or polymers such as, for example, poly(alpha-hydroxyesters), poly(ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or copolymers, terpolymers thereof or blends of those polymers, or a combination of biocompatible and biodegradable materials. One can also use biodegradable glass and bioactive glass self-reinforced and ultrahigh strength bioabsorbable composites assembled from partially crystalline bioabsorbable polymers, like polyglycolides, polylactides and/or glycolide/lactide copolymers.

The biocompatible polymer may be shaped using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the RUG. Next a solvent is used to dissolve away one of the components, resulting in pore formation. (See Mikos, U.S. Pat. No. 5,514,378, hereby incorporated by reference). In nucleation, thin films in the shape of a RUG are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a RUG structure with uniform pore sizes. Coating refers to coating or permeating a polymeric structure with a material such as, for example liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix may be weaved, compression molded and glued together. Furthermore different polymeric materials shaped by different processes may be joined together to form a composite shape. The composite shape may be a laminar structure. For example, a polymeric matrix may be attached to one or more polymeric matrixes to form a multilayer polymeric matrix structure. The attachment may be performed by gluing with a liquid polymer or by suturing. In addition, the polymeric matrix may be formed as a solid block and shaped by laser or other standard machining techniques to its desired final form. Laser shaping refers to the process of removing materials using a laser.

Figure 15:
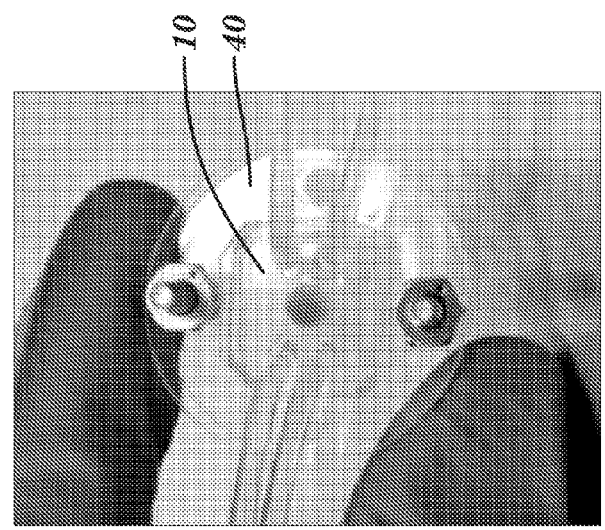
FIG. 15 depicts an implantation device after the in vivo implantation stage is complete and the implantation device has been removed from the first subject, with bone marrow tissue visible in the center of the implantation device, and coupled to a microfluidic system.

In some embodiments, the chip 10, comprising one or more layers, can be mounted onto or between one or more acrylic plates 40. The acrylic plate(s) can have one or more holes to permit microfluidic tubes access to the ports 12, 14 of the chip 10. Alternatively, the acrylic plate can have a central opening that does not cover the entire surface of the chip 10. The acrylic plates can be connected using screws, bolts, pins, adhesives or any other fastener known in the art. By way of non-limiting example, in the embodiment depicted in FIG. 15, the chip 10 can be placed between two acrylic plates 40. Each acrylic plate 40 depicted in FIG. 15 can be 25 mm in diameter and 2 mm in thickness. The acrylic plates 40 can protect the chip 10 from damage and/or contamination. The acrylic plates 40 can be of a size and shape to mount in a microfluidic system.

Methods

In accordance with various embodiments of the technology described herein, the chip described herein can be filled with a hydrogel, such as a collagen gel, mixed with other agents or formulations to induce, attract and/or support cell migration and/or colonization in the cell growth chamber. In some embodiments, the cells colonizing the cell growth chamber can be stem cells. In some embodiments, the cells colonizing the cell growth chamber can be progenitor cells. In some embodiments, the stem and/or progenitor cells colonizing the cell growth chamber can differentiate and give rise to one or more differentiated cell types. In some embodiments, the cells colonizing the cell growth chamber can form tissue structures or miniature organ structures. The cell and/or tissue types which can colonize or arise from stem cells within the cell growth chamber include, but are not limited to, mesenchymal stem cells, adipose-derived stem cells, endothelial stem cells, hematopoietic stem cells, bone cells, bone marrow cells, liver cells, blood cells, adipose cells, muscle cells, stem cells, vascular cells, immune cells, differentiated cells, diseased cells, connective tissue, muscle tissue, nervous tissue, and/or epithelial tissue.

In some embodiments, the hydrogel can include compositions which enhance or stimulate bone growth. In some embodiments these compositions can include demineralized bone powder and/or the proteins bone-morphogenic protein 2 (BMP-2) (SEQ ID NO: 01, NCBI ID NO: NP001191.1) and/or BMP-4 (SEQ ID NO: 02, NCBI ID NO: NP_001193, NP_570911, and NP_570912). In some embodiments these compositions can include demineralized bone powder and/or the proteins BMP-2 and/or BMP-4 and optionally, other bone-inducing material, i.e. a material such as a small molecule, peptide, or protein that contributes to providing a matrix for cell growth, attracting cell migration into the implantation device, promoting cell growth, promoting bone cell growth, promoting bone marrow cell growth, promoting bone cell differentiation, promoting bone marrow cell differentiation, promoting bone tissue growth, and/or promoting bone marrow tissue growth. In some embodiments, the gel mixture can be placed in the ports, in the fluid channels and/or in the cell growth chamber. In some embodiments, the bone-inducing material can be placed in the cell growth chamber and the collagen can be placed in the ports. In some embodiments, the bone-inducing material can be placed in the cell growth chamber and the fluid channels and the collagen can be placed in the ports.

Demineralized bone powder can be obtained commercially. Alternatively, demineralized bone powder can be prepared by excising, fragmenting, and sieving mouse femurs to obtain particles less than 250 µm in diameter. The powder can then be demineralized using 0.5 N HCl.

An exemplary hydrogel gel mixture can be prepared using Type I collagel gel (3 mg/mL), demineralized bone powder (0.1 mg/uL), BMP-2 (5 ng/uL), and BMP-4 (5 ng/uL). BMP-2 and BMP-4 are available commercially from Sigma Aldrich (St. Louis Mo.; Catalog Numbers B3555 and B2680 respectively).

In other embodiments, the tissue grown in the chip can be a hematopoietic or immune system tissue, including for example, bone marrow, lymph nodes, or spleen and the collagen gel can include compositions which enhance or stimulate the growth of, for example, lymph node or spleen tissue. In some embodiments these compositions can include interleukins, chemokines, interferons, tumor necrosis factor, hematopoietins, granulocyte colony-stimulating factor (G-CSF) and granulocyte-macrophage colony-stimulating factor (GM-CSF).

In other embodiments, the tissue grown in the chip can be, for example, connective tissue, vascular tissue, or fascial type structures and the collagen gel can include compositions which enhance or stimulate the growth of, for example, connective tissue, vascular tissue, or fascial type structures. In some embodiments these compositions can include VEGF (Cat #V7259, Sigma Aldrich, St. Louis, Mo.) and PDGF (Cat #P8147, Sigma Aldrich, St. Louis, Mo.).

In accordance with some embodiments of the technology described herein, the chip can then be implanted in a subject. In some embodiments, the chip can be implanted subcutaneously. In some embodiments, the chip can be implanted intraperitoneally. In some embodiments, the chip can be implanted intramuscularly. In some embodiments, the chip can be sutured to muscle at the subcutaneous site. The chip can be provided with one or more holes to allow passage of a suture needle and/or thread through the implantation device. In a preferred embodiment, the chip can be placed such that the open side(s) and/or ports of the cell growth chamber face the underlying muscle tissue of the subject.

In some embodiments, the in vivo implantation phase can last at least 1 week, at least 2 weeks, at least 4 weeks, at least 6 weeks, at least 8 weeks, at least 10 weeks, or longer. The time duration of the implantation phase can be determined as function of the desired amount of migration and colonization of cells in the cell growth chamber or area. This can be dependent on the subject and the composition of collagen gel or other mixture provided in the cell growth chamber or area.

In some embodiments, it is believed that when the chip is implanted subcutaneously, wound healing processes result in connective tissues containing microcapillaries, mesenchymal stem cells, stem cells, vascular cells, immune cells, differentiated cells, and/or diseased cells growing into the cell growth chambers of the implantation device, and due to the presence of the bone-inducing material, can form bone with spaces that recruit circulating hematopoietic precursor cells to form fully functional bone marrow.

In some embodiments, a chip 10 can be implanted in a subject. In some embodiments, an implantation device comprising part of a complete microfluidic chip, for example, the middle layer 30 of a chip 10 can be implanted in a subject. In some embodiments, an implantation device which does not comprise part of a complete microfluidic chip, for example, device having the structure of a middle layer 30 (e.g. a cartridge), but which is not later coupled to further structures to constitute a complete microfluidic chip can be implanted in a subject. In some embodiments, the implantation device can be implanted in the subject and after the in vivo growth period is concluded, the implantation device can be coupled to a microfluidic system without removing the cells, tissues and/or organoid from the implantation device and/or chip. In some embodiments, the implantation device can be implanted in the subject and after the in vivo growth period is concluded, the cells, tissues, and/or organoid can be removed from the implantation device and placed in a microfluidic device which can be coupled to a microfluidic system. In some embodiments, the implantation device can be implanted in the subject and after the in vivo growth period is concluded, the implantation device can be transplanted to a subject without removing the cells, tissues and/or organoid from the implantation device. In some embodiments, the implantation device can be implanted in the subject and after the in vivo growth period is concluded, the cells, tissues, and/or organoid can be removed from the implantation device and transplanted in a subject.

In Vitro/Ex Vivo Methods

Some embodiments of the technology described herein relate to forming a functional organ composed of two or more physiologically and structurally integrated tissues during the in vivo implantation phase and maintaining these structural and functional relationships during at least part of the in vitro and/or ex vivo phase as described below herein.

In accordance with some embodiments of the technology described herein, when the in vivo implantation phase is to be ended, the chip can be removed from the subject and placed in or connected to a microfluidic system. In some embodiments, the microfluidic system can be used to provide continuous medium perfusion, for example, using the one or more fluid channels, to develop and/or maintain cell and tissue viability. In some embodiments the chip can be removed from the site of implantation and then connected to a microfluidic system where perfusion begins. In other embodiments, the chip can be connected to a microfluidic system prior to removal from the site of implantation and perfusion begun at any time prior to complete detatchment of the chip and the tissue contained therein from the tissue of the implantation site.

In some embodiments, the chip can be placed into a nutrient-rich medium after removal from the site of implantation in order to transport the chip to a microfluidic system.

In accordance with some embodiments, the cells present in the chip can be cultured under continuous perfusion conditions and can differentiate and/or produce more tissue. In alternative embodiments, the cells can be cultured using a wide range of perfusion profiles and conditions as desired to control the development and maintenance of the cultured cells. In accordance with some embodiments, the cells present in the chip can be cultured under continuous perfusion conditions and can differentiate into bone marrow and/or produce more bone marrow tissue. In some embodiments, the viability of the cells present in the chip can be maintained through perfusion until the implantation device is implanted into a second subject.

Appropriate media for perfusion, which may also be used as the nutrient-rich medium for transport of the chip, are commercially available and a medium appropriate for the particular tissue being grown in the chip would be well known to one skilled in the art. The medium can be supplemented with, for example, additional nutrients, antibiotics, growth factors or other compounds which enhance the growth of the desired cells in vitro. By way of example only, an appropriate medium for growth of liver tissue can be Dulbecco's Modified Eagle's Medium (DMEM) containing 10% (v/v) fetal bovine serum (FBS), 100 U/mL penicillin, and 100 U/mL streptomycin while an appropriate medium for the growth of bone marrow can be MyeloCul M5300 Medium (Stem Cell Technologies) containing non-Essential Amino Acid (Gibco) Sodium Pyrvate (Gibco), 100 U/mL penicillin, and 100 U/mL streptomycin.

In some embodiments the cells and/or tissue grown in the chip can be utilized in vitro to produce cells or stem cells for therapeutic or research purposes. In some embodiments the cells and/or tissue grown in the chip can be utilized in vivo to produce hematopoietic cells or hematopoietic stem cells for therapeutic or research purposes. In some embodiments, the hematopoietic cells can be selected from the group consisting of red blood cells, white blood cells, platelets, hematopoietic stem cells, lymphocytes, eosinophils, neutrophils, monocytes, hematopoietic progenitor cells, stromal cells, and a mixture of two or more of these cell types. In some embodiments, the cells can be collected from the effluent of the chip. In some embodiments, the cells can be collected by removing the cells and/or tissue from the cell growth chamber 22. In some embodiments, the cells can be utilized for therapeutic or research purposes while present in the chip.

In some embodiments, growth factors or compounds that enhance the production of the desired cell type(s) can be added to the perfusion fluid. By way of non-limiting example, erythropoietin stimulates the production of red blood cells, VEGF stimulates angiogenesis, and thrombopoietin stimulates the production of megakaryocytes and platelets.

Cells produced according to the methods described herein can be used for therapeutic or research purposes without further manipulation or can be manipulated prior to their final use. By way of non-limiting example, manipulation of the cells can include sorting according to cell type, expanding in culture, mixing with other components of a pharmaceutical composition, contacting the cells with a compound that alters the state, function, or functionality of the cell (i.e. nucleic acid, a protein, a peptide, and/or a small molecule), freezing, and/or refrigeration.

In some embodiments, the methods and devices directed to production of a chip containing tissue and/or cells can also be used to investigate the response of cells and/or tissue, such as for example, bone marrow tissue and/or hematopoietic cells, to some compounds (e.g. chemotherapies or radiation therapies). In some embodiments, the chip containing tissue and/or cells can also be used to investigate the mechanisms involved in control of differentiation, formation, survival, growth, function, and/or remodeling of cells, tissues and/or organ structures. In these embodiments, it can be desirable to deliver some compounds to the cells in the cell growth chamber at predefined time intervals or delivery profiles (according to predefined concentrations, quantities and time intervals) via the fluid channels (e.g. hormones such as thrombopoietin which regulates production of platelets or erythropoietin which controls red blood cell production). Compounds which can be delivered to the cells in the cell growth chamber via the fluid channel(s) include, but are not limited to, hormones, enzymes, cells, gene silencing molecules, inhibitors of some enzymes, small molecules, peptides, proteins, nucleotides, antibodies, growth factors, viruses, bacteria, parasites, markers and/or dyes.

In some embodiments, the tissue and/or cells present in the chip can be used to screen compounds for toxicity. In some embodiments, the bone marrow tissue and/or hematopoietic cells present in the chip can be used to screen compounds for toxicity to bone marrow. In some embodiments, the tissue and/or cells present in the chip can be used to screen compounds for an ability to increase the growth, development and/or function of the tissue or a component thereof. In some embodiments, the bone marrow tissue and/or hematopoietic cells present in the chip can be used to screen compounds for an ability to increase the growth, development, survival, growth and/or function of bone marrow or a component thereof. In some embodiments, the tissue and/or cells present in the chip can be used to screen compounds for an ability to inhibit the growth, survival, development and/or function of the tissue or a component thereof. In some embodiments, the bone marrow tissue and/or hematopoietic cells present in the chip can be used to screen compounds for an ability to inhibit the growth, survival, development and/or function of bone marrow or a component thereof. In some embodiments, the bone marrow tissue and/or hematopoietic cells present in the chip can be used to screen compounds for an ability to mobilize some cells and/or non-cellular products from the bone marrow. In some embodiments, the bone marrow tissue and/or hematopoietic cells present in the chip can be used to screen compounds for an ability to inhibit the mobilization of some cells and/or non-cellular products from the bone marrow. In some embodiments, the tissue and/or cells present in the chip can be used to screen compounds for suitability as imaging agents for the tissue or a component thereof. In some embodiments, the bone marrow tissue and/or hematopoietic cells present in the chip can be used to screen compounds for suitability as imaging agents for bone marrow or a component thereof. In some embodiments, the tissue and/or cells present in the chip can be used to characterize the pharmacokinetics of a drug or lead compound. In some embodiments, the bone marrow tissue and/or hematopoietic cells present in the chip can be used to characterize the pharmacokinetics of a drug or lead compound. In some embodiments, the tissue and/or cells present in the chip can be used to study the microenvironment, architecture, function and/or development of that tissue type. In some embodiments, the bone marrow tissue and/or hematopoietic cells present in the chip can be used to study the microenvironment, architecture, function and/or development of bone marrow.

In some embodiments, the tissue and/or cells present in the chip can be used to produce cells, and/or non-cellular factors or compounds produced by the tissue for use in additional in vitro systems and/or models. In some embodiments, the bone marrow tissue and/or hematopoietic cells present in the chip can be used to produce blood cells, immune cells, other bone marrow-derived cells, and/or non-cellular factors or compounds produced by bone marrow for use in additional in vitro systems and/or models. By way of non-limiting example, a bone marrow-derived factor can be a peptide, protein, small molecule, nucleotide, lipid, carbohydrate, cytokine and/or growth factor. By way of non-limiting example, the response of liver tissue to compounds can include an immune component which is absent in in vitro models of liver tissue Immune cells produced by the bone marrow cells and/or tissue present in the chip can be delivered to an in vitro model of liver tissue in order to constitute a more complete model of liver function and response. In some embodiments the products of bone marrow can be collected from the chip as described elsewhere herein and added to an additional in vitro system and/or model. In some embodiments, the chip containing the bone marrow can be located in the same microfluidic system as the additional in vitro model and/or system. The perfusion fluid can be passed through the chip containing the bone marrow and the effluent, containing the products of bone marrow, can be delivered to the additional in vitro model and/or system. The chip containing the bone marrow can be upstream, downstream, or both with respect to the additional in vitro model and/or system. All or part of the effluent of the chip containing bone marrow can be delivered to the additional in vitro model and/or system.

In some embodiments, the methods and devices described herein can be used to study or produce cells and/or tissue at a particular stage of development. By varying the time of implantation, the identities and concentrations of tissue-inducing material, the design of the chip, and the composition of the perfusion fluid, the stage of development of the cells and/or tissue present on the chip can be varied. In some embodiments this can be used to study, for example, the process of bone marrow development, the function of bone marrow constituents at some points of development, the differential effects of compounds on bone marrow over the course of development and/or the effects of compounds on development of bone marrow. By way of non-limiting example, the compound can be a chemotherapeutic, radiation therapy, modifier of differentiation, formation, function or remodeling, hormone, nucleic acid, peptide, protein, antibody, small molecule, drug lead, enzyme, cell, virus, bacterium, parasite, nucleotide, marker, dye, imaging agent, enzyme, nanoparticle, and/or gene silencing molecule.

In some embodiments, the tissue and/or cells present in the chip can be human cells and/or tissue without having been implanted in a human. In these embodiments, the chip can be implanted into an animal having human and/or humanized cells. By way of non-limiting example, a mouse can be irradiated to eliminate its endogenous bone marrow and then be given a graft of human bone marrow and/or human hematopoietic stem cells. When a chip is implanted, whether before, during or after the above-mentioned procedures, it will ultimately be populated by human bone marrow cells. When removed from the site of implantation and placed in a microfluidic system, the bone marrow contained in the chip will be genetically human. The bone marrow produced in this manner can be used in any of the embodiments described herein.

In some embodiments, the source of the xenografted human cells is a cancer tumor or cancerous tissue and/or cells. In some embodiments the suitable types of cancers can include, but are not limited to, leukemia, lymphoma, Hodgkin's lymphoma, myeloproliferative disorders, Langerhans cell histiocytosis, myeloma, and myelodysplastic syndromes. In some embodiments, the xenografted human cells can be obtained from diseased tissue. In some embodiments, the xenografted human cells can be obtained from a human having a hematopoietic disease. Hematopoietic diseases include, but are not limited to thalassemia, factor IX deficiency, hemophilia, sickle cell disease, amyloidosis, agranulocytosis, anemia, leucopenia, neutropenia, thrombocytopenia, panctyopenia, Glanzmann's thrombasthenia, uremia, platelet storage pool disease, Von Willebrand disease, afibrinogenemia and auto-immune disease.

In some embodiments, when the chip is removed from the first subject, some or all of the cells present in the chip can be removed from the chip. By way of non-limiting example, bone marrow cells that have colonized the bone marrow niche in the chip can be removed by chemical and/or physical means. Cells in the cell growth chamber of a chip can be removed from the chip and/or made nonviable by any method known in the art for partially or completely decellularizing a tissue. Non-limiting examples include 1) washing the chip and/or tissue with detergents or 2) washing the chip with a buffer, then fixing the tissue with paraformaldehyde. In some embodiments, the chip and/or tissue can be decellularized by fixing with 4% paraformaldehyde (PFA) for 48 hours at 4° C. and then immersing the chip and/or tissue in 70% ethanol for 24 hours at 4° C. and three times in PBS at 4° C. for 2 hours each time to wash out the PFA. In some embodiments, the internal marrow cavity of the chip can be removed by cutting a small opening at the edge of the cavity and flusing with medium.

The remaining decellularized bone marrow scaffold can be used ex vivo and/or in vitro and be repopulated by bone marrow and/or blood cells provided from another source. The tissue grown in vivo in the chip and the second population of cells can be from different species, e.g. the chip can be implanted in a mouse and decellularized ex vivo, then repopulated with human bone marrow cells.

In Vivo Methods

In some embodiments, the chip containing the tissue and/or cells, or the tissue and/or cells removed from the chip, after being removed from the first subject, can be implanted into a second subject (e.g. human or animal) and used in vivo. In some embodiments, the chip containing the tissue and/or cells, or the tissue and/or cells removed from the chip can be implanted into a second subject subcutaneously. Any amount of tissue and/or cells from the chip can be used in vivo, e.g. from 0.1% to 100% of the tissue and/or cells in the chip can be used in vivo. For example, at least 0.1% of the tissue or cells in the chip, at least 1% of the tissue or cells in the chip, at least 10% of the tissue or cells in the chip, at least 50% of the tissue or cells in the chip, at least 90% of the tissue or cells in the chip, or at least 95% or more of the tissue or cells in the chip can be used in vivo. The tissue and/or cells can be selected and/or separated prior to in vivo use by, for example, cell sorting (e.g. FACS) or physical separation of a portion of the tissue and/or cells.

In some embodiments, both the first and second subjects can be animals. In some embodiments, both the first and second subjects can be non-human animals of the same species, e.g. both subjects can be mice. In some embodiments, both the first and second subjects can be human. In some embodiments, the first and second subjects can be the same subject. In some embodiments, the first and second subjects can be of different species, e.g. the first subject can be a mouse and the second subject can be a human.

In some embodiments, a chip can be implanted into a mouse having human and/or humanized cells. After a period of in vivo growth, the chip containing the tissue and/or cells, or the tissue and/or cells removed from the chip can be transplanted to a human in need of a transplant of the type of cells grown in the chip. In some embodiments, a chip can be implanted into a mouse having human and/or humanized bone marrow or hematopoietic cells. After a period of in vivo growth, the chip is transplanted to a human in need of a transplant of bone marrow and/or hematopoietic cells.

In some embodiments, the recipient (e.g. second) subject can have a cancer, a hematopoietic disease, radiation toxicity, or a compromised immune system. In some embodiments, the recipient subject can have undergone chemotherapy or radiation therapy. In some embodiments, the recipient is a subject diagnosed as having a hematologic disease in which one or more of the blood cell types found in the bone marrow are rendered dysfunctional. In some embodiments, the recipient is a human who received a treatment that damaged, compromised, or eliminated their endogenous bone marrow. Such treatments can include, for example chemotherapy, radiation therapy. In some embodiments, the human may be one who was exposed to a source of radiation or a chemical, pollutant or infection that damaged, compromised, or eliminated their endogenous bone marrow. Examples of such chemicals, pollutants, or infections include, but are not limited to, alcohol, benzene, hepatitis, Epstein-Barr virus, cytomegalovirus, parvovirus B19 and HIV.

In further embodiments, tissue and/or stem cells can be removed from a human prior to them receiving a treatment that will damage, compromise, or eliminate that tissue and/or cell type. By way of non-limiting example, bone marrow tissue and/or hematopoietic stem cells can be removed from a human prior to them receiving a treatment that will damage, compromise, or eliminate their bone marrow. The bone marrow tissue and/or hematopoietic stem cells removed from the human can be implanted into an immunocompromised animal. A chip implanted in such a mouse will be colonized by bone marrow tissue and/or hematopoietic cells that are genetically identical to the human and the chip, after a period of in vivo growth in the animal, can be implanted into the human, or the cells and/or tissue contained in the chip can be implanted into the human, thereby supplying a source of bone marrow tissue and/or hematopoietic cells that is genetically identical to the human. In some embodiments, the chip or the cells and/or tissue contained in the chip can be stored, preserved, or maintained after removing them from the site of implantation in the mouse and before transplanting them to the human. In some embodiments, the chip or the cells and/or tissue can be preserved by freezing. In some embodiments, the chip or the cells and/or tissue can be preserved by refrigeration. In some embodiments, the cells contained in the chip can be maintained by removing the chip from the site of implantation and connecting it to a microfluidic system as described elsewhere herein. Perfusion fluid can be provided via the microfluidic system and the cells contained in the chip maintain their viability until it is desired to transplant the chip or the bone marrow tissue and/or hematopoietic cells into the human.

In some embodiments, a chip can be implanted into a subject. After a period of in vivo growth, the chip can be connected to a microfluidic system and the tissue and/or cells contained on the chip can be maintained by perfusion of a fluid as described herein. After removal of the chip from the site of implantation, the subject receives a treatment that damages, compromises, or eliminates the cell and/or tissue type that was grown on the chip. After such a treatment is concluded, the chip containing the tissue and/or cells, or the tissue and/or cells removed from the chip can be implanted into the subject, thereby supplying a source of tissue and/or cells that is genetically identical to the subject. By way of non-limiting example, after a period of in vivo growth where bone growth was induced in the chip, the chip can be connected to a microfluidic system and the bone marrow tissue and/or hematopoietic cells contained on the chip can be maintained by perfusion of a fluid as described herein. After removal of the chip from the site of implantation, the subject receives a treatment that damages, compromises, or eliminates their endogenous bone marrow. After such a treatment is concluded, the chip containing the bone marrow tissue and/or hematopoietic cells, or the bone marrow tissue and/or hematopoietic cells removed from the chip can be implanted into the subject, thereby supplying a source of bone marrow tissue and/or hematopoietic cells that is genetically identical to the subject.

In some embodiments, the chip or the tissue and/or cells contained in the chip can be stored, preserved, or maintained after removing them from the site of implantation in the first subject and before returning them to the second subject and/or after removing them from the site of implantation in the first subject and before returning them to the first subject. In some embodiments, the chip or the cells and/or tissue can be preserved by freezing. In some embodiments, the chip or the cells and/or tissue can be preserved by refrigeration. In some embodiments, the cells contained in the chip can be maintained by removing the chip from the site of implantation and connecting it to a microfluidic system as described elsewhere herein. Perfusion fluid can be provided via the microfluidic system and the cells contained in the chip maintain their viability until it is desired to transplant the chip or the bone marrow tissue and/or hematopoietic cells into the human. In some embodiments, a chip and/or the tissue and/or cells contained in the chip can be subject to multiple methods of maintaining, storing, or preserving the cells and/or tissue ex vivo, e.g. the tissue in a chip can be cultured in a microfluidics device and then frozen and subsequently thawed before being transplanted into a recipient subject.

In some embodiments, the chip and/or the tissue and/or cells contained in the chip can be transplanted directly from the first subject to the second subject without maintaining, storing, and/or preserving the cells and/or tissue ex vivo.

In some embodiments, the tissue and/or cells contained within the implantation device are genetically modified before implantation into the second subject. In some embodiments, the device is colonized by cells that are genetically modified, e.g. the first subject comprises genetically modified cells. In some embodiments, the first subject is a transgenic subject. In some embodiments, the tissue and/or cells are genetically modified after the implantation device and the tissue and/or cells contained therein are removed from the first subject. In some embodiments, the tissue and/or cells are genetically modified after the tissue and/or cells are removed from the implantation device. In some embodiments, the tissue and/or cells are genetically modified while the tissue and/or cells are being maintained or cultured in a microfluidic device or system. By way of non-limiting example, tissue and/or cells can be genetically modified to increase or decrease gene expression or to express an exogenous gene (e.g. a marker gene). Methods of genetically modifying tissue and/or cells are well known in the art and can include, but are not limited to, viral vectors, plasmid vectors, homologous recombination, stable integration, and transient expression.

Pharmaceutical Compositions

For administration to a subject, the chip containing cells and/or tissue or the cells and/or tissue contained within the chip or products of the cells and/or tissue contained within the chip can be provided in pharmaceutically acceptable compositions. These pharmaceutically acceptable compositions comprise the chip, cells, tissues, and/or products of the cells or tissues, as described above, formulated together with one or more pharmaceutically acceptable carriers (additives) and/or diluents. As described in detail below, the pharmaceutical compositions of the technology described herein can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, lotion, gel, ointment, or a controlled-release patch or spray applied to the skin; (4) intravaginally or intrarectally, for example, as a pessary, cream, suppository or foam; (5) sublingually; (6) ocularly; (7) transdermally; (8) transmucosally; or (9) nasally. Additionally, compositions can be implanted into a patient or injected using a drug delivery system. Coated delivery devices can also be useful. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; U.S. Pat. No. 6,747,014; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include, but are not limited to: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, binding agents, fillers, lubricants, coloring agents, disintegrants, release agents, coating agents, sweetening agents, flavoring agents, perfuming agents, preservative, water, salt solutions, alcohols, antioxidants, polyethylene glycols, gelatin, lactose, amylose, magnesium stearate, talc, silicic acid, viscous paraffin, hydroxymethylcellulose, polyvinylpyrrolidone and the like can also be present in the formulation. The terms such as "excipient", "carrier", "pharmaceutically acceptable carrier" or the like are used interchangeably herein.

Many organized surfactant structures have been studied and used for the formulation of drugs. These include monolayers, micelles, bilayers and vesicles. Vesicles, such as liposomes, have attracted great interest because of their specificity and the duration of action they offer from the standpoint of drug delivery. Liposomes are unilamellar or multilamellar vesicles which have a membrane formed from a lipophilic material and an aqueous interior. The aqueous portion contains the composition to be delivered. Liposomes can be cationic (Wang et al., Biochem. Biophys. Res. Commun., 1987, 147, 980-985), anionic (Zhou et al., Journal of Controlled Release, 1992, 19, 269-274), or nonionic (Hu et al. S.T.P. Pharma. Sci., 1994, 4, 6, 466). Liposomes can comprise a number of different phospholipids, lipids, glycolipids, and/or polymers which can impart specific properties useful in some applications and which have been described in the art (Allen et al., FEBS Letters, 1987, 223, 42; Wu et al., Cancer Research, 1993, 53, 3765; Papahadjopoulos et al. Ann. N.Y. Acad. Sci., 1987, 507, 64; Gabizon et al. PNAS, 1988, 85, 6949; Klibanov et al. FEBS Lett., 1990, 268, 235; Sunamoto et al. Bull. Chem. Soc. Jpn., 1980, 53, 2778; Illum et al. FEBS Lett., 1984, 167, 79; Blume et al. Biochimica et Biophysica Acta, 1990, 1029, 91; U.S. Pat. Nos. 4,837,028; 5,543,152; 4,426,330; 4,534,899; 5,013,556; 5,356,633; 5,213,804; 5,225,212; 5,540,935; 5,556,948; 5,264,221; 5,665,710; European Patents EP 0 445 131 B1; EP 0 496 813 B1; and European Patent Publications WO 88/04924; WO 97/13499; WO 90/04384; WO 91/05545; WO 94/20073; WO 96/10391; WO 96/40062; WO 97/0478).

The compositions of the technology described herein can be prepared and formulated as emulsions or microemulsions. Emulsions are typically heterogeneous systems of one liquid dispersed in another in the form of droplets usually exceeding 0.1 μm in diameter and have been described in the art. Microemulsion can be defined as a system of water, oil and amphiphile which is a single optically isotropic and thermodynamically stable liquid solution and can comprise surfactants and cosurfactants. Both of these drug delivery means have been described in the art (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 199, 245, & 335; Higuchi et al., in Remington's Pharmaceutical Sciences, Mack Publishing Co., Easton, Pa., 1985, p. 301; Leung and Shah, in: Controlled Release of Drugs: Polymers and Aggregate Systems, Rosoff, M., Ed., 1989, VCH Publishers, New York, pages 185-215; Schott, in Remington's Pharmaceutical Sciences, Mack Publishing Co., Easton, Pa., 1985, p. 271; Constantinides et al., Pharmaceutical Research, 1994, 11, 1385-1390; Ritschel, Meth. Find. Exp. Clin. Pharmacol., 1993, 13, 205; Ho et al., J. Pharm. Sci., 1996, 85, 138-143; Lee et al., Critical Reviews in Therapeutic Drug Carrier Systems, 1991, p. 92; U.S. Pat. Nos. 6,191,105; 7,063,860; 7,070,802; 7,157,099).

In one embodiment, the liposome or emulsion formulation comprises a surfactant. Surfactants find wide application in formulations such as emulsions (including microemulsions) and liposomes. The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285). Suitable surfactants include fatty acids and/or esters or salts thereof, bile acids and/or salts thereof. In some embodiments the surfactant can be anionic, cationic, or nonionic. The use of surfactants in drug products, formulations and in emulsions has been reviewed (Rieger, in Pharmaceutical Dosage Forms, Marcel Dekker, Inc., New York, N.Y., 1988, p. 285).

In some embodiments, the technology described herein employs various penetration enhancers to effect the efficient delivery of compounds across cell membranes. Penetration enhancers can be classified as belonging to one of five broad categories, i.e., surfactants, fatty acids, bile salts, chelating agents, and non-chelating non-surfactants all of which have been described elsewhere (see e.g., Malmsten, M. Surfactants and polymers in drug delivery, Informa Health Care, New York, N.Y., 2002; Lee et al., Critical Reviews in Therapeutic Drug Carrier Systems, 1991, p. 92; Takahashi et al., J. Pharm. Pharmacol., 1988, 40, 252; Touitou, E., et al. Enhancement in Drug Delivery, CRC Press, Danvers, Mass., 2006; Muranishi, Critical Reviews in Therapeutic Drug Carrier Systems, 1990, 7, 1-33; El Hariri et al., J. Pharm. Pharmacol., 1992, 44, 651-654; Brunton, Chapter 38 in: Goodman & Gilman's The Pharmacological Basis of Therapeutics, 9th Ed., Hardman et al. Eds., McGraw-Hill, New York, 1996, pp. 934-935; Swinyard, Chapter 39 In: Remington's Pharmaceutical Sciences, 18th Ed., Gennaro, ed., Mack Publishing Co., Easton, Pa., 1990, pages 782-783; Yamamoto et al., J. Pharm. Exp. Ther., 1992, 263, 25; Yamashita et al., J. Pharm. Sci., 1990, 79, 579-583; Jarrett, J. Chromatogr., 1993, 618, 315-339; Katdare, A. et al., Excipient development for pharmaceutical, biotechnology, and drug delivery, CRC Press, Danvers, Mass., 2006; Buur et al., J. Control Rel., 1990, 14, 43-51)

Oral formulations and their preparation are described in detail in U.S. Pat. No. 6,887,906, US Publn. No. 20030027780, and U.S. Pat. No. 6,747,014, each of which is incorporated herein by reference. Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients. Aqueous suspensions can further contain substances which increase the viscosity of the suspension including, for example, sodium carboxymethylcellulose, sorbitol and/or dextran. The suspension can also contain stabilizers.

Aerosols for the delivery to the respiratory tract are known in the art. See for example, Adjei, A. and Garren, *J. Pharm. Res.*, 1: 565-569 (1990); Zanen, P. and Lamm, J.-W. J. *Int. J. Pharm.*, 114: 111-115 (1995); Gonda, I. "Aerosols for delivery of therapeutic an diagnostic agents to the respiratory tract," in *Critical Reviews in Therapeutic Drug Carrier Systems*, 6:273-313 (1990); Anderson et al., *Am. Rev. Respir. Dis.*, 140: 1317-1324 (1989)) and have potential for the systemic delivery of peptides and proteins as well (Patton and Platz, *Advanced Drug Delivery Reviews*, 8:179-196 (1992)); Timsina et. al., *Int. J. Pharm.*, 101: 1-13 (1995); and Tansey, I. P., *Spray Technol. Market*, 4:26-29 (1994); French, D. L., Edwards, D. A. and Niven, R. W., *Aerosol Sci.*, 27: 769-783 (1996); Visser, J., *Powder Technology* 58: 1-10 (1989)); Rudt, S, and R. H. Muller, J. *Controlled Release*, 22: 263-272 (1992); Tabata, Y, and Y. Ikada, *Biomed. Mater. Res.*, 22: 837-858 (1988); Wall, D. A., *Drug Delivery*, 2: 10 1-20 1995); Patton, J. and Platz, R., *Adv. Drug Del. Rev.*, 8: 179-196 (1992); Bryon, P., *Adv. Drug. Del. Rev.*, 5: 107-132 (1990); Patton, J. S., et al., *Controlled Release*, 28: 15 79-85 (1994); Damms, B. and Bains, W., *Nature Biotechnology* (1996); Niven, R. W., et al., *Pharm. Res.*, 12(9); 1343-1349 (1995); and Kobayashi, S., et al., Pharm. Res., 13(1): 80-83 (1996), contents of all of which are herein incorporated by reference in their entirety.

The compositions of the technology described herein can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the technology described herein, such as dyes, flavoring agents, preservatives, antioxidants, opacifiers, thickening agents and stabilizers. However, such materials, when added, should not unduly interfere with the biological activities of the components of the compositions of the technology described herein. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the compound(s) of the formulation.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The technology described herein is further illustrated by the following examples which should not be construed as limiting.

Some embodiments of the technology described herein can be defined as any of the following numbered paragraphs:
1. A method of maintaining tissue ex vivo, the method comprising:
    implanting an implantation device in a subject whereby the implantation device is colonized by at least one of stem cells, vascular cells, immune cells, differentiated cells and diseased cells;
    removing the implantation device and the tissue contained in the implantation device from the subject;
    providing a perfusion fluid to the tissue.
2. The method of paragraph 1, further comprising the step of removing the tissue from the implantation device prior to providing perfusion fluid.
3. The method of paragraph 2, further comprising the step of placing the tissue in a microfluidic system prior to providing perfusion fluid.
4. The method of any of paragraphs 1-3, wherein the implantation device includes at least one cell growth chamber and at least one open port providing a passage to the cell growth chamber to enable cells to enter the cell growth chamber for cell colonization.
5. The method of paragraph 1, wherein the implantation device is a microfluidic device.
6. The method of paragraph 5, further comprising connecting the microfluidic device to a microfluidic system.
7. The method of any of paragraphs 5-6, wherein the microfluidic device includes at least one cell growth chamber and at least one open port providing a passage to the cell growth chamber to enable cells to enter the cell growth chamber for cell colonization.
8. The method of any of paragraphs 5-7, wherein the microfluidic device includes at least one fluid channel separated from the at least one cell growth chamber by a porous separation component.

9. The method of any of paragraphs 5-8, wherein the microfluidic device includes at least one inlet port and at least one outlet connecting the at least one fluid channel to the microfluidic system and providing perfusion fluid to the at least one cell growth chamber through the porous separation component.

10. The method of any of paragraphs 1-9, wherein the implantation device is implanted such that at least one port faces the muscle tissue of the subject.

11. The method of any of paragraphs 1-10, wherein the tissue is bone marrow tissue.

12. The method of any of paragraphs 1-12, wherein the bone marrow tissue maintained ex vivo is used to produce hematopoietic cells or bone marrow-derived factors.

13. The method of paragraph 12, wherein the hematopoietic cells are selected from the group consisting of red blood cells, white blood cells, platelets, hematopoietic stem cells, lymphocytes, eosinophils, neutrophils, monocytes, hematopoietic progenitor cells, stromal cells, and a mixture of two or more of these cell types.

14. The method of paragraph 12, wherein the bone marrow-derived factors are selected from the group consisting of a peptide, protein, small molecule, nucleotides, lipids, carbohydrates, cytokines and growth factors.

15. The method of any of paragraphs 12-14, wherein the hematopoietic cells and/or bone marrow-derived factors are administered to a subject.

16. The method of paragraph 15, wherein the subject has a condition selected from the group consisting of a compromised immune system, a cancer, an auto-immune disease, radiation toxicity, and a hematopoietic disease.

17. The method of paragraph 16, wherein the cancer is selected from the group consisting of leukemia, lymphoma, Hodgkin's lymphoma, myeloproliferative disorders, Langerhans cell histiocytosis, myeloma, and myelodysplastic syndromes.

18. The method of paragraph 16, wherein the hematopoietic disease is selected from the group consisting of thalassemia, factor IX deficiency, hemophilia, sickle cell disease, amyloidosis, agranulocytosis, anemia, leucopenia, neutropenia, thrombocytopenia, panctyopenia, Glanzmann's thrombasthenia, uremia, platelet storage pool disease, Von Willebrand disease, and afibrinogenemia.

19. The method of paragraph 15, wherein the subject has undergone chemotherapy and/or radiation therapy.

20. The method of paragraph 12, wherein the hematopoietic cells and/or bone marrow-derived factors are provided to another tissue type being maintained in vitro.

21. The method of any of paragraphs 1-11, wherein the tissue maintained ex vivo is used to test the effect of compounds on the tissue or interaction of compounds with the tissue, where the compound is selected from the group consisting of chemotherapeutics, radiation therapies, modifiers of differentiation, formation, function or remodeling, hormones, nucleic acids, peptides, proteins, antibodies, small molecules, drug leads, enzymes, cells, viruses, bacteria, parasites, nucleotides, markers, dyes, imaging agents, enzymes, nanoparticles, and gene silencing molecules.

22. The method of any of paragraphs 1-11, wherein the tissue maintained ex vivo is at any stage of development.

23. The method of any of paragraphs 1-22, wherein the implantation device is implanted into a non-human subject.

24. The method of any of paragraphs 1-22, wherein the implantation device is implanted into a non-human subject having human or humanized hematopoietic cells.

25. The method of paragraph 24, wherein the non-human subject has human hematopoietic cells obtained from a cancer or a human having a hematopoietic disease.

26. The method of paragraph 25, wherein the cancer is selected from the group consisting of leukemia, lymphoma, Hodgkin's lymphoma, myeloproliferative disorders, Langerhans cell histiocytosis, myeloma, and myelodysplastic syndromes.

27. The method of paragraph 25, wherein the hematopoietic disease is selected from the group consisting of thalassemia, factor IX deficiency, hemophilia, sickle cell disease, amyloidosis, agranulocytosis, anemia, leucopenia, neutropenia, thrombocytopenia, panctyopenia, Glanzmann's thrombasthenia, uremia, platelet storage pool disease, Von Willebrand disease, and afibrinogenemia.

28. A method of producing tissue or cells for implantation into a subject, the method comprising: implanting an implantation device in a first subject whereby the implantation device is colonized by tissue or cells; removing the implantation device and the tissue contained in the implantation device from the first subject;
transplanting the implantation device or at least the tissue or cells contained in the implantation device into a second subject thereby providing tissue or cells to the second subject;
whereby the implanted tissue or cells exhibit cell growth and function in the second subject.

29. The method of paragraph 28, wherein the implantation device includes at least one cell growth chamber and at least one open port providing a passage to the cell growth chamber to enable cells to entire the cell growth chamber for cell colonization.

30. The method of paragraph 28, wherein the implantation device is a microfluidic device.

31. The method of paragraph 30, wherein the microfluidic device includes at least one cell growth chamber and at least one open port providing a passage to the cell growth chamber to enable cells to enter the cell growth chamber for cell colonization.

32. The method of any of paragraphs 30-31, wherein the microfluidic device includes at least one fluid channel separated from the at least one cell growth chamber by a porous separation component.

33. The method of any of paragraphs 30-32, wherein the microfluidic device includes at least one inlet port and at least one outlet connecting the at least one fluid channel to the microfluidic system and providing perfusion fluid to the at least one growth channel through the porous separation component.

34. The method of any of paragraphs 28-33, wherein the implantation device is implanted such that at least one port faces the muscle tissue of the subject.

35. The method of any of paragraphs 28-34, wherein the tissue or cells comprise bone marrow tissue or hematopoietic cells.

36. The method of any of paragraphs 28-35, wherein the second subject receiving the transplant has been diagnosed with a condition selected from the group consisting of a compromised immune system, a cancer, an auto-immune disease, and a hematopoietic disease.

37. The method of paragraph 36, wherein the cancer is selected from a group consisting of leukemia, lymphoma, Hodgkin's lymphoma, myeloproliferative disorders, Langerhans cell histiocytosis, myeloma, and myelodysplastic syndromes.
38. The method of paragraph 36, wherein the hematopoietic disease is selected from the group consisting of thalassemia, factor IX deficiency, hemophilia, sickle cell disease, amyloidosis, agranulocytosis, anemia, leucopenia, neutropenia, thrombocytopenia, panctyopenia, Glanzmann's thrombasthenia, uremia, platelet storage pool disease, Von Willebrand disease, and afibrinogenemia.
39. The method of any of paragraphs 28-38, wherein the second subject has undergone chemotherapy and/or radiation therapy.
40. The method of any of paragraphs 28-39, wherein the implantation device is implanted into a non-human first subject having human or humanized hematopoietic cells.
41. The method of any of paragraphs 28-40, wherein the first and second subjects are the same individual and the method comprises an additional step of maintaining either the implantation device containing bone marrow tissue and/or hematopoietic cells or the bone marrow tissue or hematopoietic cells after removal from the implantation device between removal from the site of implantation and transplantation into the subject.
42. The method of any of paragraphs 28-40, wherein the method comprises an additional step of maintaining either the implantation device containing bone marrow tissue and/or hematopoietic cells or the bone marrow tissue or hematopoietic cells after removal from the implantation device between removal from the site of implantation and transplantation into the second subject.
43. The method of any of paragraph 28-42, wherein maintaining the implantation device containing bone marrow tissue or hematopoietic cells ex vivo comprises freezing or refrigerating either the implantation device containing bone marrow tissue and/or hematopoietic cells or the bone marrow tissue and/or hematopoietic cells after removal from the implantation device.
44. The method of any of paragraphs 28-42, wherein maintaining the implantation device containing bone marrow tissue or hematopoietic cells ex vivo comprises:
connecting the implantation device to a microfluidic systems;
providing a perfusion fluid to the implantation device.
45. The method of any of paragraphs 28-45, wherein the tissue or cells contained within the implantation device are genetically modified before implantation into the second subject.
46. A pharmaceutical composition comprising bone marrow tissue, hematopoietic cells, or differentiated blood cells obtained from a bone marrow tissue maintained ex vivo according to the method of paragraph 1.
47. A pharmaceutical composition comprising bone marrow tissue and/or hematopoietic cells obtained from a bone marrow tissue maintained ex vivo according to the method of paragraph 28.
48. The composition of any of paragraphs 46-47, wherein the bone marrow tissue and/or hematopoietic cells are contained within an implantation device.
49. A method for producing or manufacturing hematopoietic cells, the method comprising implanting an implantation device in a subject whereby the implantation device is colonized by stem cells, vascular cells, immune cells or differentiated cells;
removing the implantation device and the tissue contained in the implantation device from the subject;
providing a perfusion fluid to the tissue;
wherein the implantation device includes at least one cell growth chamber and at least one open port providing a passage to the cell growth chamber to enable cells to enter the cell growth chamber for cell colonization;
wherein the tissue is bone marrow tissue;
and wherein the bone marrow tissue maintained ex vivo is used to produce hematopoietic cells.
50. The method of paragraph 49, wherein the hematopoietic cells are selected from the group consisting of red blood cells, white blood cells, platelets, hematopoietic stem cells, lymphocytes, eosinophils, neutrophils, monocytes, a hematopoietic progenitor cell, and a mixture of two or more of these cell types.

EXAMPLES

Example 1: Well Format Implantation Devices

Figure 4A:
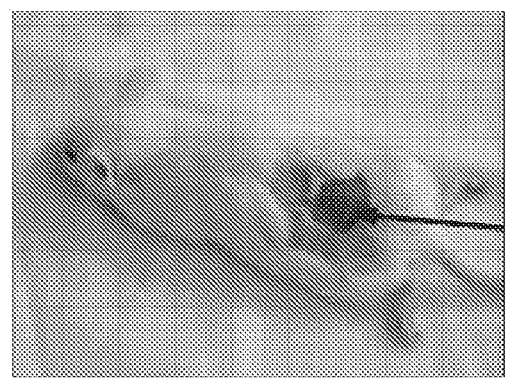
FIGS. 4A-4C show photographs depicting the subcutaneous implantation of an implantation device in a mouse.
Figure 4B:
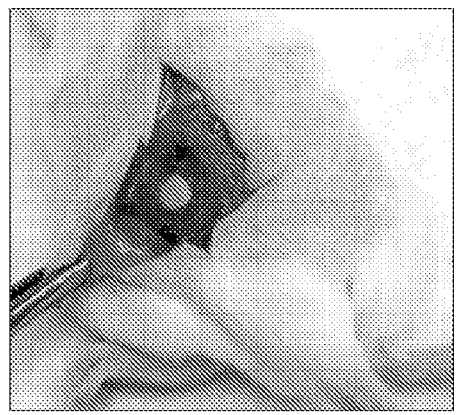
Figure 4C:
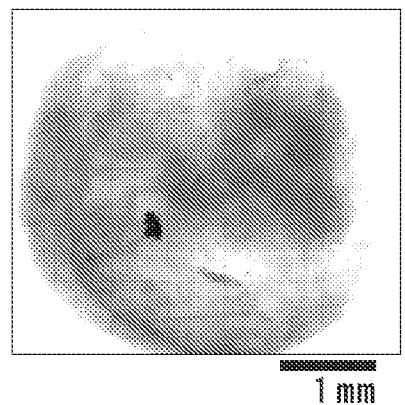

In vivo culturing of bone tissue in an implantation device was first investigated using a chip as shown in FIG. 3C, i.e. a Well Format implantation device having two openings. The well was filled with a collagen gel mixture comprising Type I collagen, demineralized bone powder, BMP-2, and BMP-4 as described herein. The implantation device was then implanted subcutaneously in a mouse (FIGS. 4A-4B). Implantation devices were removed from the subject at 4 weeks or 8 weeks after implantation and the contents of the chip were examined to determine if bone marrow tissue was present in the implantation device.

Histological staining via H&E stain revealed newly generated bone marrow surrounded by a combination of new bone and the original demineralized bone powder (FIGS. 7A-7D). Staining for alkaline phosphatase activity using NBT/BCIP ready-to-use tables (cat.#11-697-471-001, Roche applied science) indicated that tissue growing in the chips contained zones of active bone formation as compared to a section of mouse femur (data not shown). In the presence of alkaline phosphatase, the BCIP (5-Bromo-4-chloro-3-indolyl phosphate, toluidine salt) is dephosphorylated and then oxidized by NBT (Nitro blue tetrazolium chloride) to yield a dark-blue indigo precipitating dye.

The presence of erythroid cells was evaluated by staining with fluorescent markers (data not shown). Erythroid cells, as detected by Ter119 staining, were found to be present in both 4-week and 8-week old in vivo grown tissues. The presence of leukocytes was evaluated by staining with fluorescent markers (data not shown). Leukocytes, as detected by CD45 staining, were found to be present in both 4-week and 8-week old in vivo grown tissues.

Figure 5:
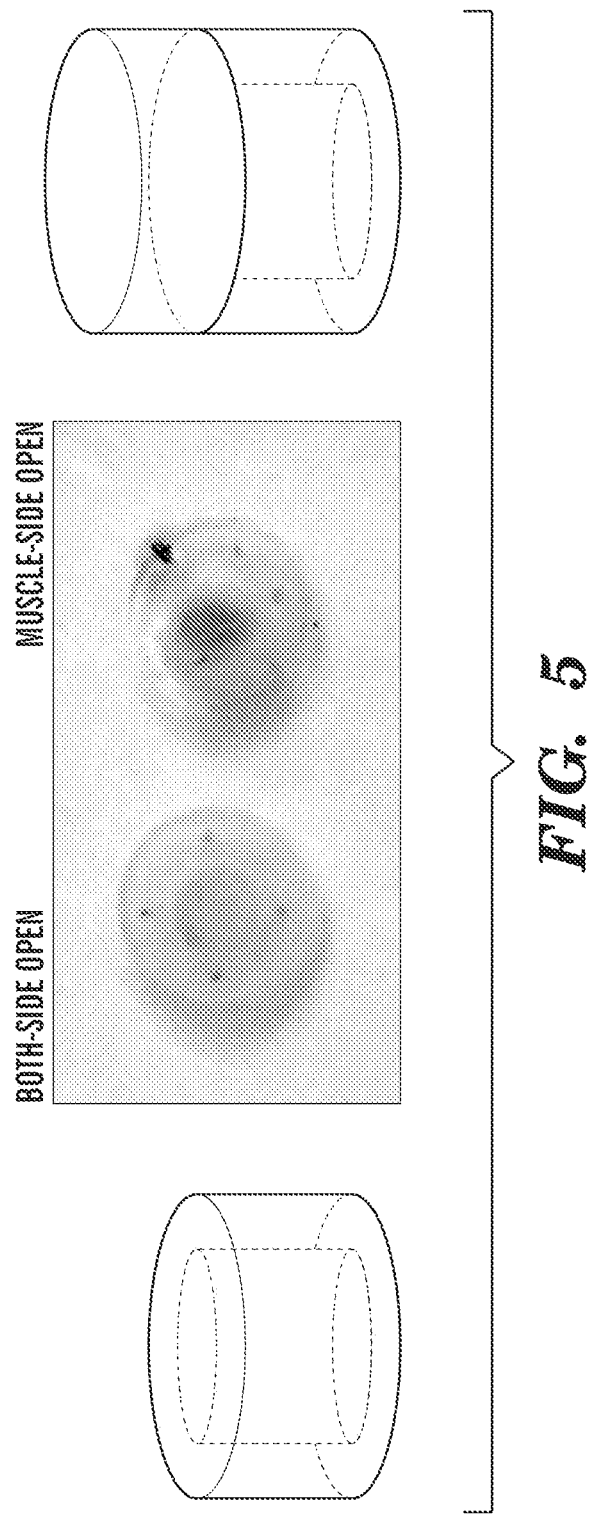
FIG. 5 shows diagrams and images of Well Format implantation devices having one opening or two openings. The photographs show the implantation devices after 4 weeks of subcutaneous in vivo growth in a mouse.
Figure 7A:
FIGS. 7A-7D show H&E stains of the contents of a Well Format implantation device with two openings 4 weeks (7A-7B) and 8 weeks (7C-7D) after implantation. Scale bars as shown.
Figure 7B:
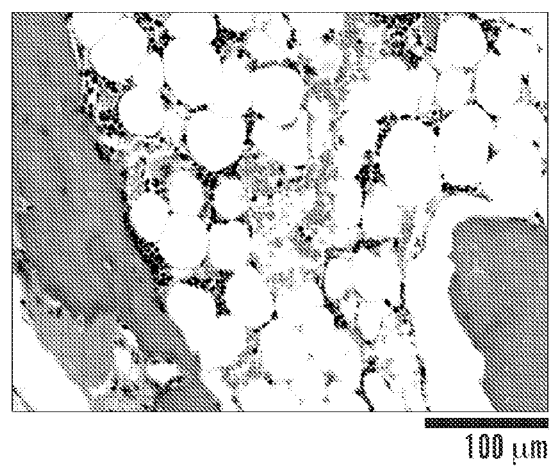
Figure 7C:
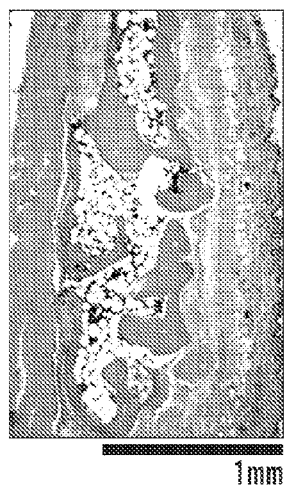
Figure 7D:
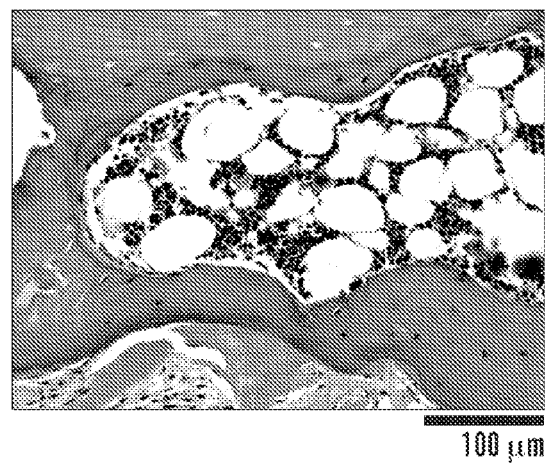

Example 2: Comparison of Well Format Implantation Devices with One or Two Openings The bone marrow in the chips with two openings was dominated by adipocytes, a cell type known to have an inhibitory effect on the hematopoietic microenvironment. To improve the quality of the engineered marrow, the polymer mold was designed to prevent infiltration of adipocytes by blocking the end of the central cavity of the polymer that faced the adipose tissue of the skin, while retaining the opening facing the muscle surface (FIG. 3D). The performance of Well Format chips having one opening or two openings was compared. The chips were filled with a collagen mixture as described herein and implanted subcutaneously in mice. FIG. 5 shows a diagram of each chip type and photographs of the chips after 4 weeks of in vivo growth. The chips were implanted subcutaneously in mice and the chips having one opening were oriented such that the opening faced the muscle of the mouse. Histological staining via H&E stain revealed newly generated bone marrow surrounded by new bone in both chip types after 8 weeks (FIGS. 6A-6C and FIGS. 7C-7D). The newly formed marrow in the chips with two openings was dominated by adipocytes and exhibited a low level of cellularity (FIGS. 7A-7D), likely because fat cells inhibit hematopoiesis (Naverias O, et al. Nature 460, 259-263 (2009)). Histological analysis of the bone marrow in the chip having one opening revealed that a thick shell of well formed bone surrounding a highly cellular marrow with a morphology nearly identical to the marrow within a femur (FIG. 16B). Micro-computed tomography (microCT) analyses show that the engineered bone marrow was surrounded by mineralized cortical bone and permeabled by trabecular bone with architectural properties similar to natural trabecular bone seen in adult mouse vertebrae (FIGS. 19A-19D).

Example 3: FACS Analysis of Implantation Device-Grown Cells

Figure 8:
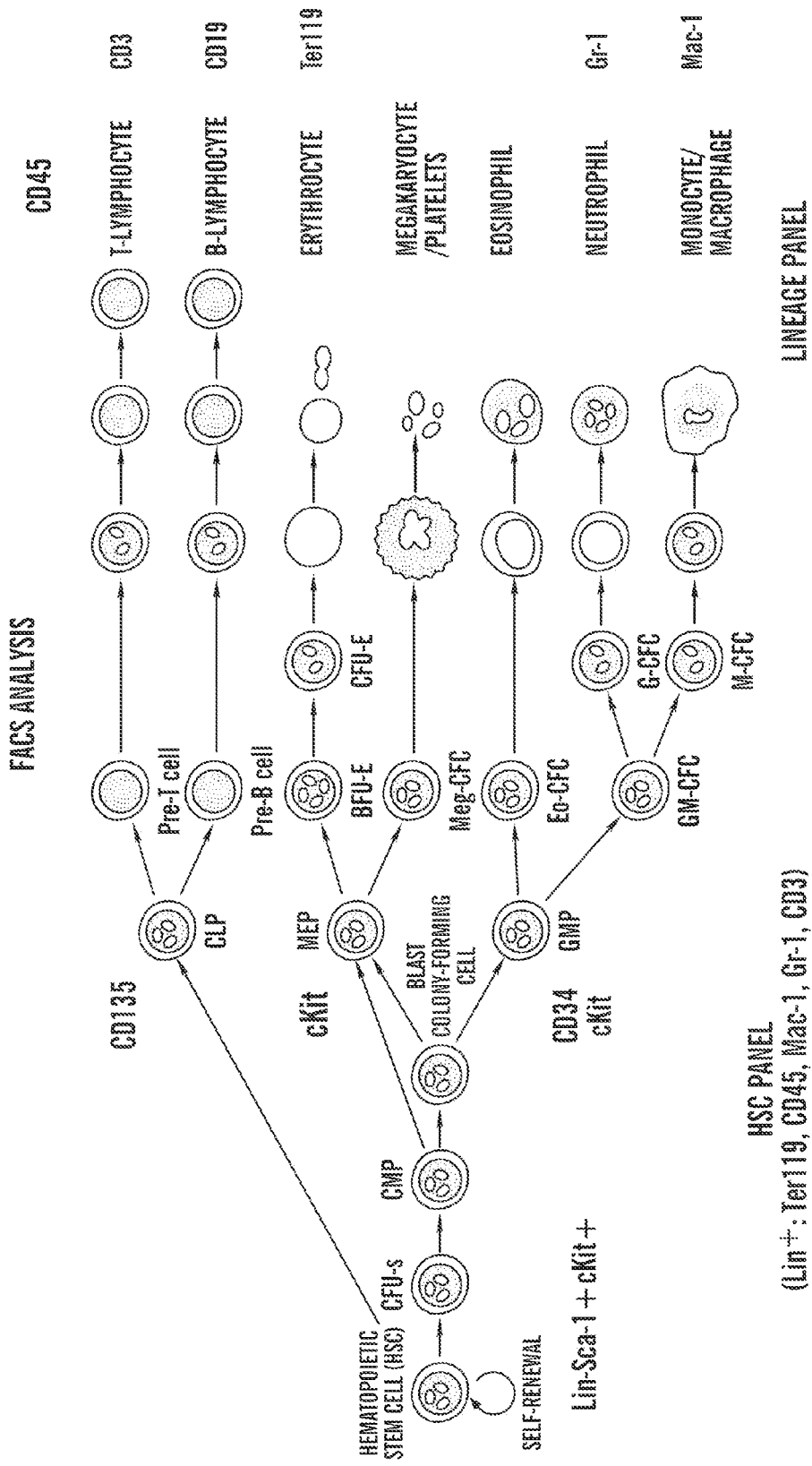
FIG. 8 shows a diagram of the hematopoietic stem cell lineage and the markers that can be used to identify each cell type.
Figure 9A:
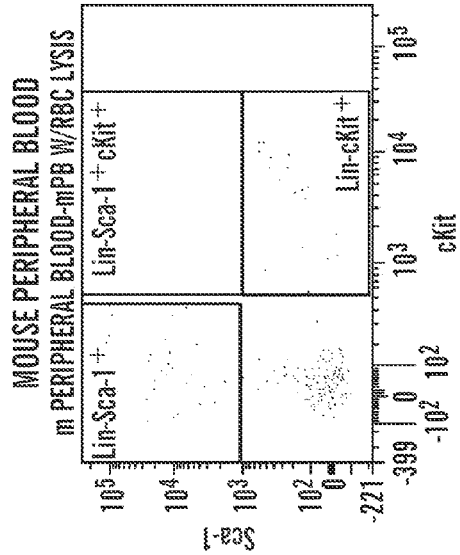
FIGS. 9A-9E show the results of FACS analysis to detect hematopoietic stem cells. 9A shows the profile obtained from mouse bone marrow (mBM), 9B shows the profile obtained from mouse peripheral blood (mPB) that the red blood cells have been lysed, 9C shows the profile obtained for tissue recovered from the implantation device after 4 weeks of in vivo growth (sBM 4 w) and 9D shows the profile obtained for tissue recovered from the implantation device after 8 weeks of in vivo growth (sBM 8w). Antibodies were used which recognized the markers indicated on x- and y-axes in FIGS. 9A-9D.
Figure 9B:
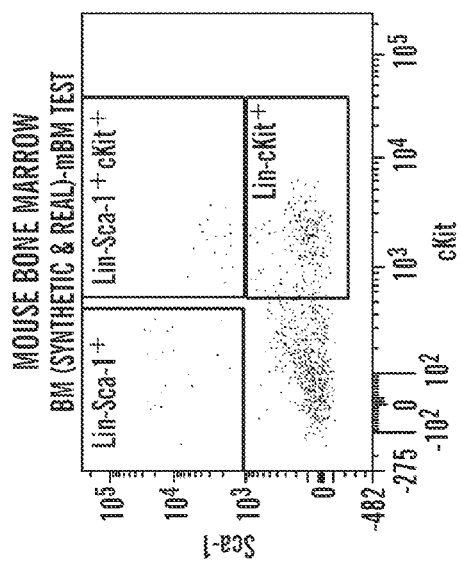
Figure 9C:
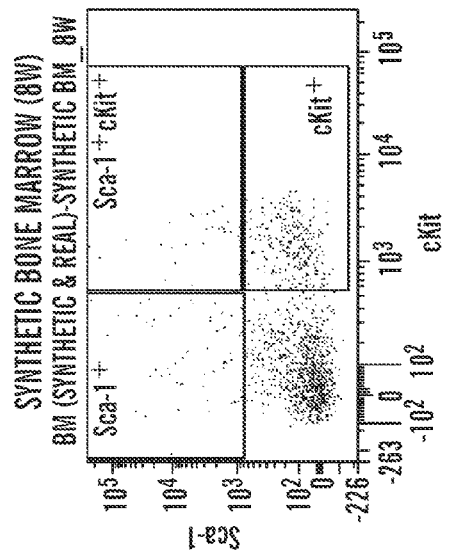
Figure 9D:
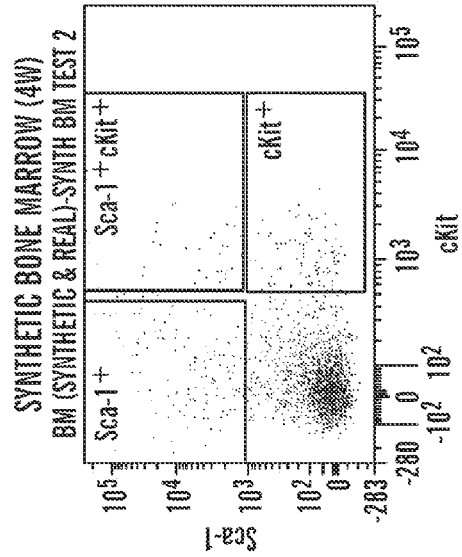
Figure 9E:
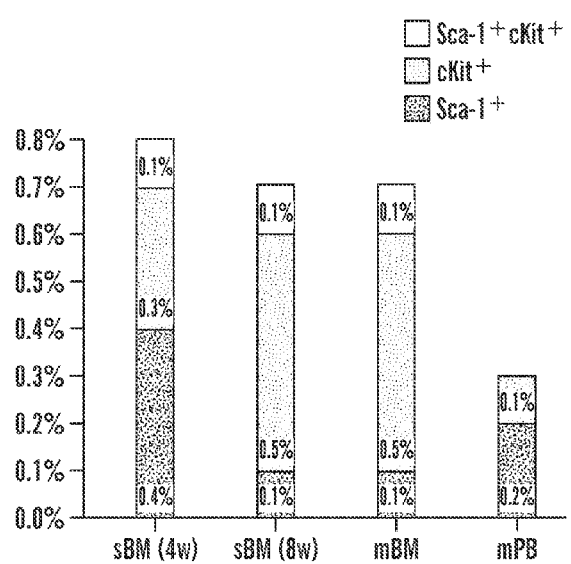
Figure 10E:
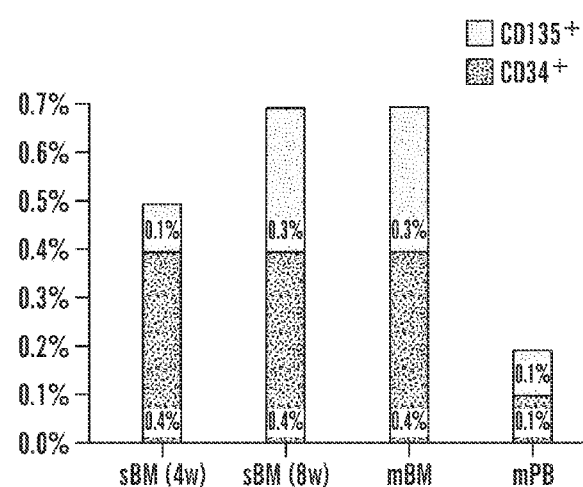
Figure 11A:
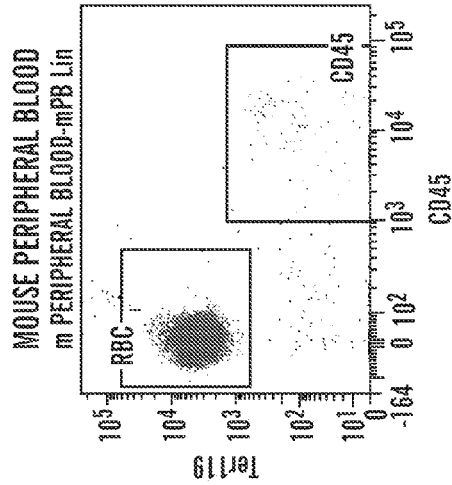
FIGS. 11A-11E show the results of FACS analysis to determine the proportion of red blood cells and leukocytes. 11A shows the profile obtained from mouse bone marrow (mBM), 11B shows the profile obtained from mouse peripheral blood (mPB), 11C shows the profile obtained from tissue recovered from the implantation device after 4 weeks of in vivo growth (sBM 4 w) and 11D shows the profile obtained from tissue recovered from the implantation device after 8 weeks of in vivo growth (sBM 8 w). Antibodies were used which recognized the markers indicated on x- and y-axes in FIGS. 11A-11D.
Figure 11B:
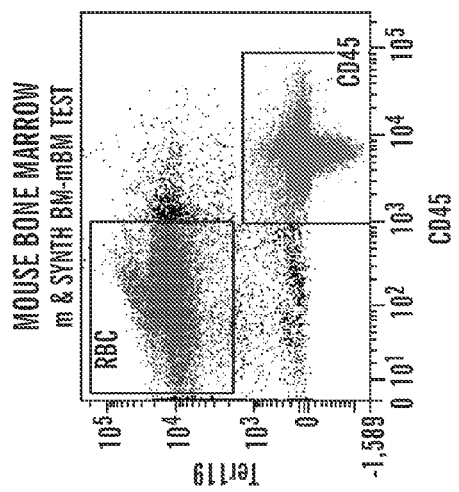
Figure 11C:
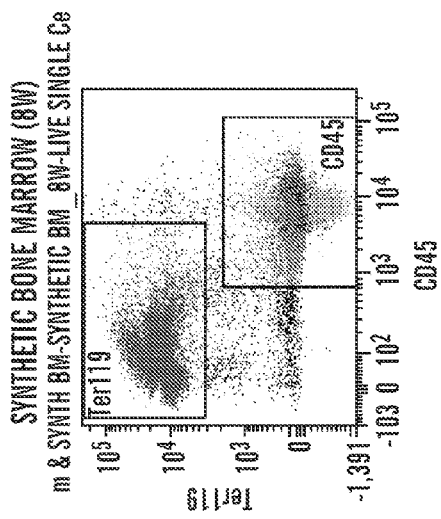
Figure 11D:
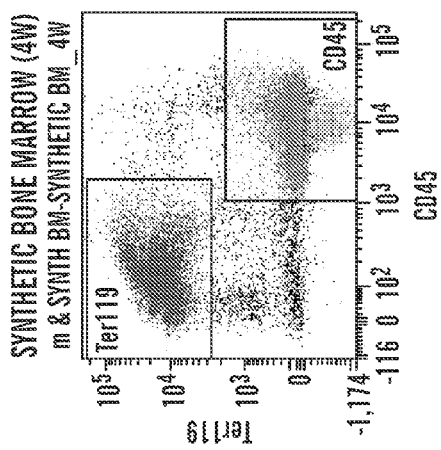
Figure 11E:
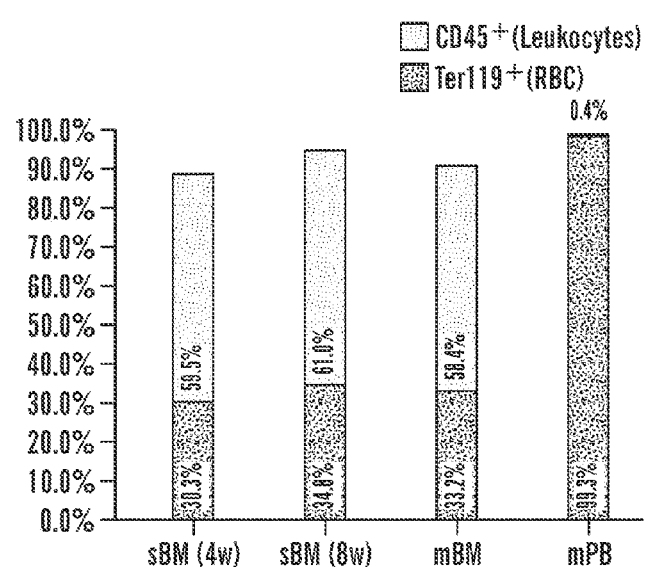
Figure 12E:
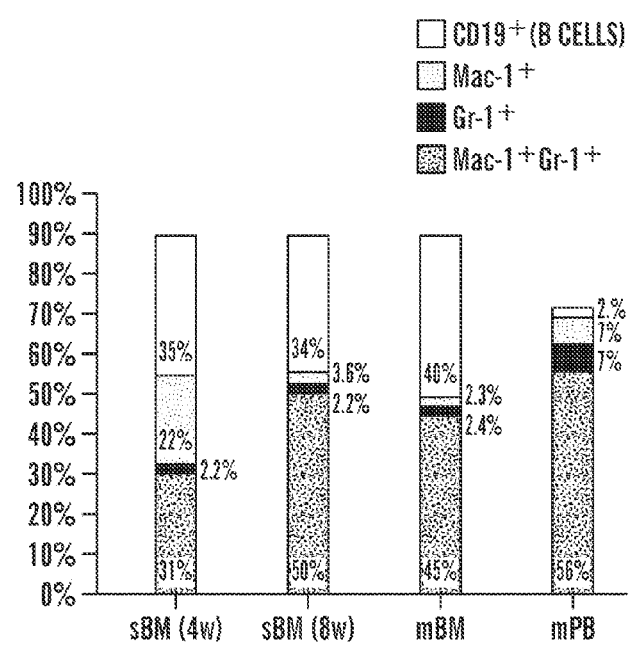

The identity of the cells growing in these chips was further investigated by FACS analysis designed to detect hematopoietic stem cells and their differentiated descendant cell types. To determine the hematopoietic cellular constitution of the bone marrow compartment, the engineered bone marrow was dissociated immediately upon surgical removal and analyzed using flow cytometry with antibodies directed against Lineage cocktail (Lin), Sca-1, c-Kit, CD34, CD135, Ter119, CD45, Mac-1, Gr-1, CD19, and CD3 to identify HSCs (Lin-c-Kit+Sca-1+), progenitor cells (Lin-c-Kit+, Lin-Sca-1+, Lin-CD34+, and Lin-CD135+), erythrocytes (Ter119+), leukocytes (CD45+, macrophages (CD45+ Mac-1+), granulocytes (CD45+Gr-1+), B cells (CD45+ CD19+), T cells (CD45+CD3+) (FIGS. 16C-16D). FIG. 8 shows the hematopoietic stem cell lineage and the markers used to detect particular cell types. The cells were grown in a Well Format chip having one opening implanted subcutaneously in a mouse such that the opening faced the muscle tissue. The chips were harvested from mice 4 weeks or 8 weeks after implantation. The tissue in the implantation devices were removed, cut into small pieces, and digested using 1 mg/mL collagenase for 30 min to harvest the cells inside the tissue. The cells were stained with antibodies as indicated and analyzed using flow cytometry. One million cells were stained with 100 µL of staining solution for 30 min. The solution was washed out and changed into sorting buffer and then the cells were analyzed using flow cytometry.

For the HSC panel the staining solution was: 20 µL mouse hematopoietic lineage eFluor 450 Cocktail, 2 µL Anti-mouse CD34 FITC, 0.3 µL Anti-mouse Ly-6A/E (Sca-1) APC, 5 µL Anti-mouse CD135 (Flt3) PE, 0.65 µL Anti-mouse CD117 (c-Kit) APC-eFluor 780, and 72 µL staining buffer. For the cell line panel the staining solution was: 2.5 µL Anti-mouse CD19 eFluor 450, 0.5 µL Anti-mouse CD45 FITC, 0.65 µL Anti-mouse Ly-6G (Gr-1) APC, 0.65 µL Anti-mouse CD11b (Mac-1) PE, 2.5 µL Anti-mouse Ter119 APC-eFluor 780, 5 µL Anti-mouse CD3 PE-Cy5 and 90 µL staining buffer. Staining buffer was 3% FBS and 0.05% sodium zide in PBS(−). Sorting buffer was 0.1% Bovine serum albumin (BSA) and 0.5% FBS in PBS(−). The antibodies were obtained from eBioscience or BD Biosciences.

For analysis of HSC in peripheral blood samples, those samples were first subjected to red blood cell lysis. Three mL of Red blood cell lysing buffer (R7757, Sigma) was added to a peripheral blood cell pellet and pipetted up and down once. After 5 min incubation at room temperature, 20 mL of PBS(−) solution was added to dilute the buffer. The buffer was removed by centrifuging (450 g for 7 min).

The tissue recovered from the chips after 4 weeks of in vivo growth (FIGS. 9C, 10C, 11C, 12C) or 8 weeks of in vivo growth (FIGS. 9D, 10D, 11D, 12D) was compared to the cellular profile of mouse bone marrow (FIGS. 9A, 10A, 11A, 12A) and peripheral blood (FIGS. 9B, 10B, 11B, 12B). The results of FACS analysis are shown in FIGS. 9A-9E, 10A-10E, 11A-11E, and 12A-12E.

Devices harvested 4 or 8 weeks after implantation contain all hematologic cell types, including hematopoietic stem and progenitor cells and both differentiated red and white blood cell lineages (FIGS. 16C-16D). While the number of hematopoietic stem and progenitor cells were lower in the engineered marrow at 4 weeks than that found in marrow from the adult mouse femur, marrow harvested from implanted devices at 8 weeks exhibited a distribution of hematopoietic stem cells, progenitors, and differentiated blood cells from all lineages nearly identical to that isolated from marrow within intact femur. These data demonstrate that the hematopoietic compartment of the engineered bone marrow faithfully recapitulates the full cellular components of natural bone marrow.

The collagen gel mixture containing demineralized bone powder and bone morphogenic proteins was able to recruit both bone and bone marrow formation from the host in the subcutaneous site. After 4 weeks of in vivo growth, bone marrow formation was observed in the implantation device and about 4 million cells could be harvested from the chip. The blood cell population formed in the implantation device was quite similar to mouse bone marrow. At 8 weeks, the chip is mostly filled with bone marrow and over 10 million cells could be harvested from the chip. The blood cell population formed in the chip was identical to mouse bone marrow. These results indicate that functional engineered bone marrow is present in the microfluidic chip after in vivo growth.

Example 4: Single Channel Format Chip

The performance of a Single Channel Format Chip (shown in FIG. 2A) was evaluated. The single closed channel was filled with demineralized bone powder, BMP-2, and BMP-4 in a collagen gel as described elsewhere herein. The ports were filled with a Type I collagen gel. The chip was implanted subcutaneously in a transgenic mouse expressing GFP. After 4 weeks of in vivo growth, the chip was removed and cell growth in the channel was examined. The channel was populated by GFP-expressing cells and after removing the bone-inducing material GFP-expressing cells remained adhered to the channel (data not shown). A large number of GFP-expressing cells were found in the channel and Ter119 staining for erythroid cells revealed their presence in the channel (data not shown). Histological examination by H&E staining also revealed growth of bone tissue (data not shown).

Example 5: Closed Channel Format Chip

The performance of a Closed Channel Format chip (shown in FIG. 2B) was also tested. The cell growth chamber was filled with demineralized bone powder, BMP-2, and BMP-4 in a collagen gel as described elsewhere herein. The ports were filled with a Type I collagen gel. The chips were implanted subcutaneously in mice and in vivo growth proceeded for 4 weeks. Chips were then removed and examined. When examined optically, dark matter was present predominantly in the cell growth chamber. The chips were stained with Hoechst DNA stain and the bright fluorescent staining revealed that cells are present at the ports and in the cell growth chamber (data not shown).

Example 6: Tumor Biopsy

Mouse lung cancer cells transduced with Cherry (red color) were injected subcutaneously into a GFP-mouse whose cells show green fluorescence. The resulting tumor formed in the mouse was harvested and then the biopsy was introduced into the cell growth chamber of the microfluidic chip as described herein. Culture medium was perfused continuously at 1 µL/min. The medium used was Dulbecco's Modified Eagle's Medium (DMEM) containing 10% (v/v) fetal bovine serum (FBS), 100 U/mL penicillin, and 100 U/mL streptomycin. When examined 5 days after biopsy, bright red fluorescence (cancer cells) and green fluorescence (mouse-derived cells) was be observed, indicating that the cancer cells and mouse-derived cells are alive (data not shown). Furthermore, the cancer cells migrated out of the middle channel, suggesting that the cancer cells continue proliferating in the microfluidic device.

Example 7: Liver Biopsy

Mouse liver was harvested and then liver biopsy was introduced into the cell growth chamber of the microfluidic chip as described herein. Culture medium was perfused continuously at 1 µL/min. The medium used was Dulbecco's Modified Eagle's Medium (DMEM) containing 10% (v/v) fetal bovine serum (FBS), 100 U/mL penicillin, and 100 U/mL streptomycin. The shape of the liver biopsy was maintained for 4 days in the cell growth chamber. Staining of the liver biopsy stained with calcein-AM (green; live cell stain) and ethidiumhomodimer (red; dead cell stain) 3 days after harvest indicated that most cells were alive after 3 days of in vitro growth (data not shown).

Example 8: Bone Marrow Transplantation

Figure 16A:
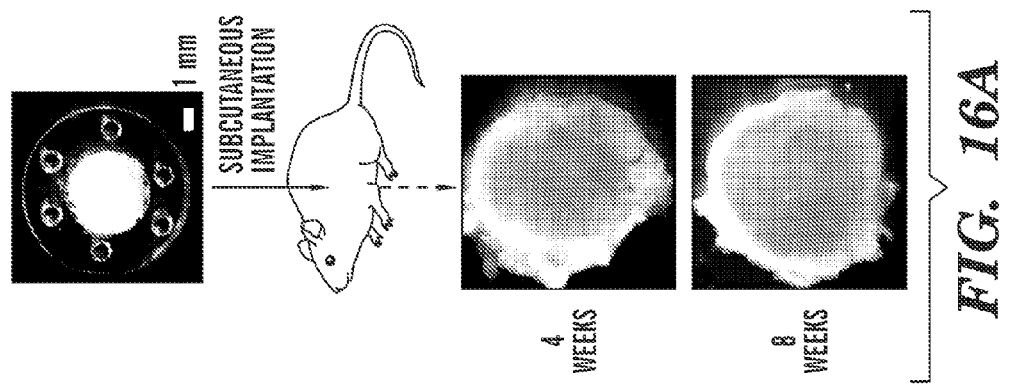
FIGS. 16A-16D depict the engineering of bone marrow by inducing bone formation in vivo. The top image in FIG. 16A depicts an implantation device filled with bone-inducing material and the growth of bone marrow after 4 and 8 weeks of implantation.
Figure 16B:
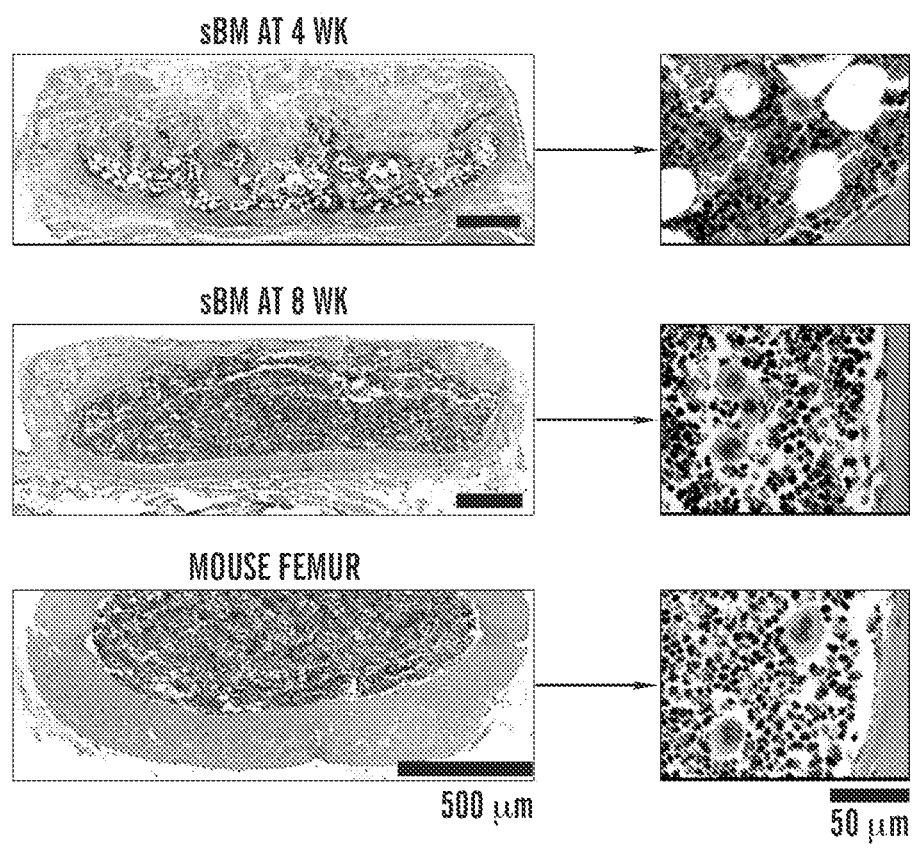
Figure 16C:
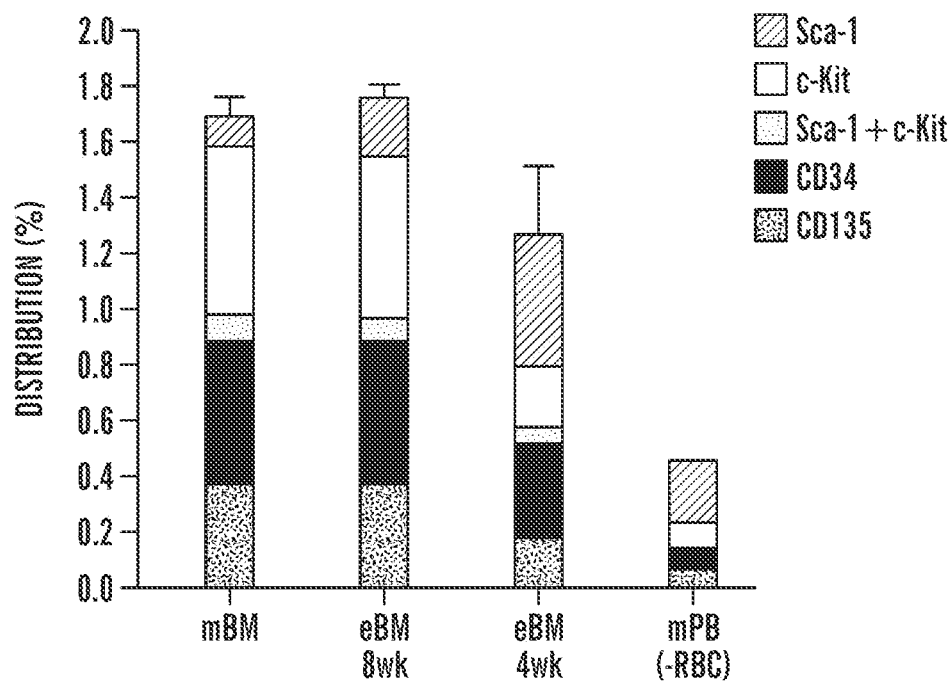
Figure 16D:
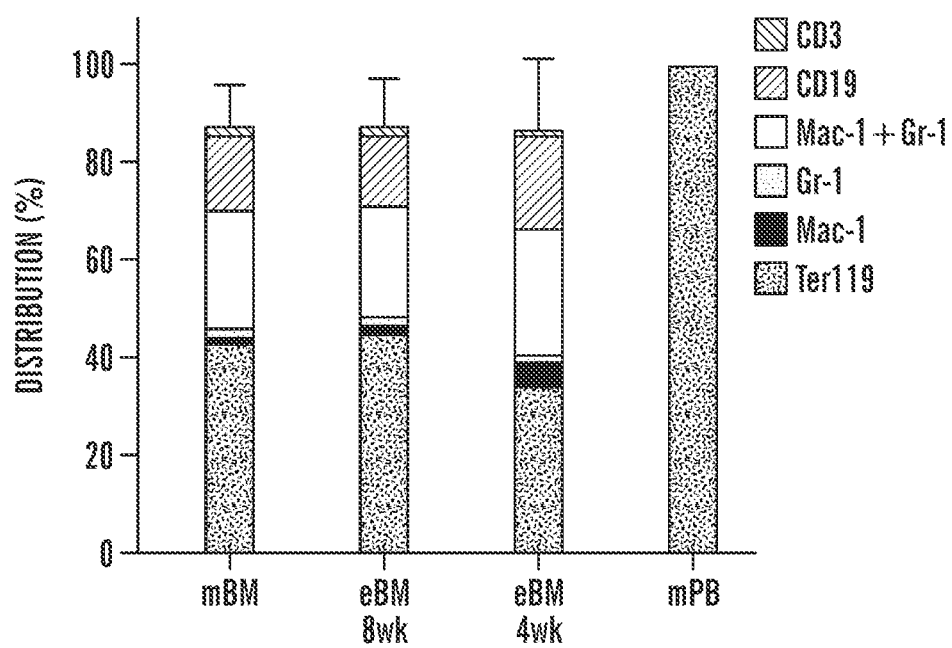
Figure 17:
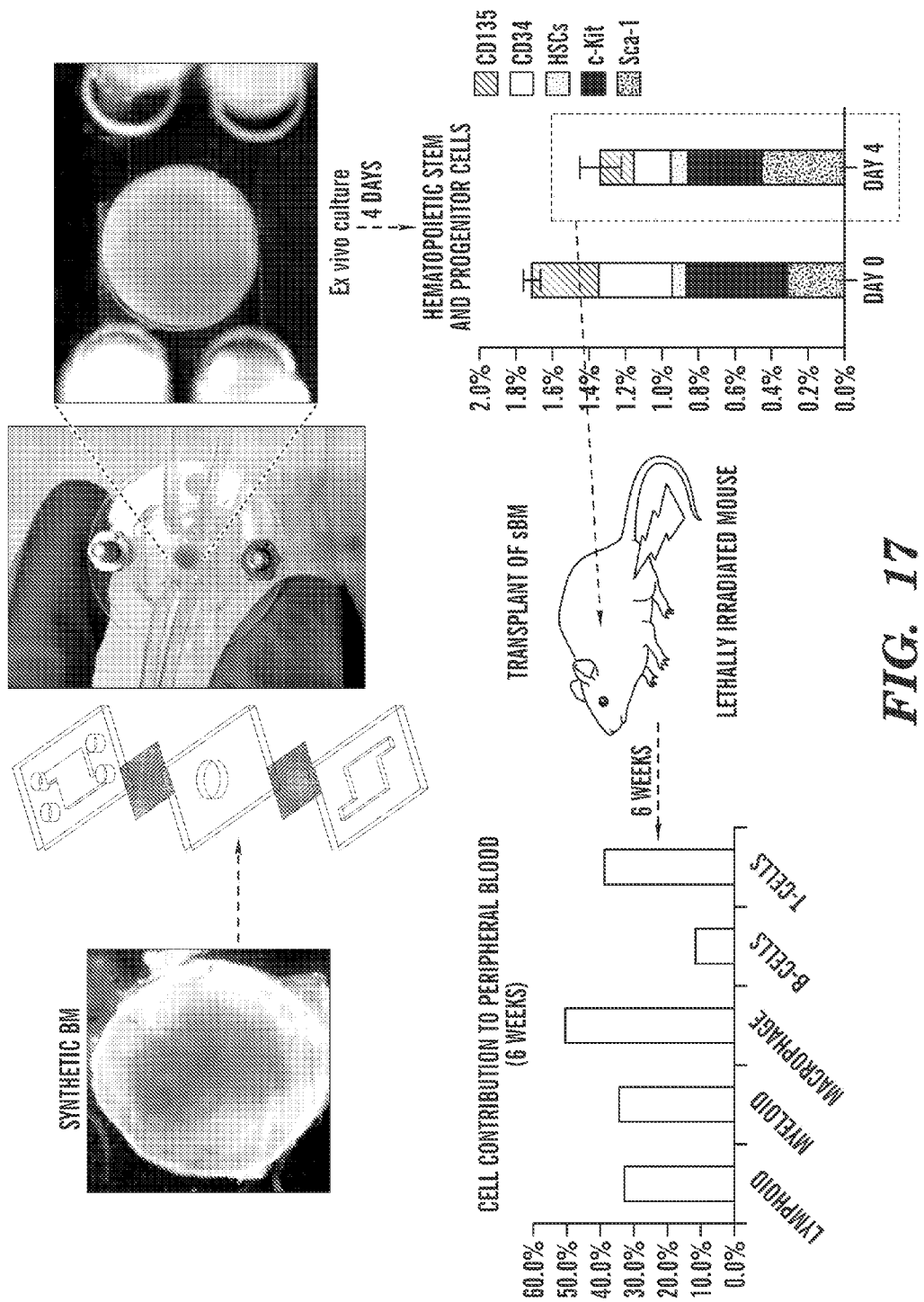
FIG. 17 depicts the microfluidic culture of synthetic bone marrow and transplantation to a lethally irradiated mouse. The bottom right graph depicts the cell type distribution of the cultured synthetic bone marrow at day 0 and day 4 of ex vivo culture. The bottom left chart shows the contribution of the transplanted bone marrow to peripheral blood populations 6 weeks after transplantation.

Bone-inducing material was implanted subcutaneously on the back of a mouse using a chip as shown in FIG. 16A and FIG. 17. After 8 weeks implantation, bone and bone marrow formed in the material. Visual examination after the device was removed from the mouse revealed a red color due to the presence of red blood cells in the tissue present in the chip.

The materials were characterized histologically (FIG. 16B). The bottom image of FIG. 16 shows the cross-section of a mouse femur. The orange color indicates bone marrow is inside of the bone tissue. The top and middle images show the cross section of the synthetic bone marrow after 4 weeks and 8 weeks implantation, respectively. Bone containing bone marrow is observed. The synthetic bone marrow is nearly identical to the mouse bone marrow. Under high magnification as shown, the cells look exactly the same.

To determine how similar the synthetic bone marrow actually is to the mouse bone marrow, the cellular distribution was analyzed using antibodies and flow cytometry. FIGS. 16C-16D show the distribution of differentiated blood cells, and hematopoietic stem and progenitor cells. After 4 days in culture, the bone marrow cells from the device were harvested and compared to cells isolated from the natural marrow of the mouse femur that were placed in a Dexter culture with a stromal cell support layer, which is the most common method currently used to maintain hematopoietic stem and progenitor cells in vitro. Flow cytometric analysis demonstrated that the distribution of hematopoietic stem and progenitor cells in the engineered bone marrow (eBM, D4) remained similar to fresh mouse femur bone marrow (FIG. 20D) whereas the composition of blood cells in the Dexter culture (mBM, D4) was strikingly different from freshly harvested mouse femur bone marrow, as previously reported. After 4 days in the Dexter culture, the proportion of long-term HSCs (Lin-CD150+CD48-staining cells) decreased and that of the hematopoietic progenitor cells (Lin-c-Kit+, Lin-Sca-1+, Lin-CD34+, and Lin-CD135+ staining cells) increased, compared to the number found in normal mouse bone marrow, suggesting the HSCs are differentiating and losing their multipotency under these conditions. In contrast, after being cultured for 4 days in the microfluidic marrow-on-a-chip, the engineered bone marrow maintained its normal distribution of HSCs as well as progenitors. These results demonstrate successfully engineered new bone marrow.

The synthetic bone marrow was cultured in a microfluidic device to keep the cells alive in vitro. Synthetic bone marrow harvested from a mouse was placed in the microfluidic device consisting of two channel layers. Culture media was perfused through the top and bottom channels. Images of the system are shown in FIG. 17. The synthetic bone marrow is placed in between the two channels and is cultured while perfusing media. After 4 days in culture, the synthetic bone marrow cells were harvested and analyzed. The bottom right graph in FIG. 17 shows the distribution of hematopoietic stem and progenitor cells. The distribution of the cells after 4 days in culture is similar to when analyzed directly after harvesting.

Figures 20A, 20B:
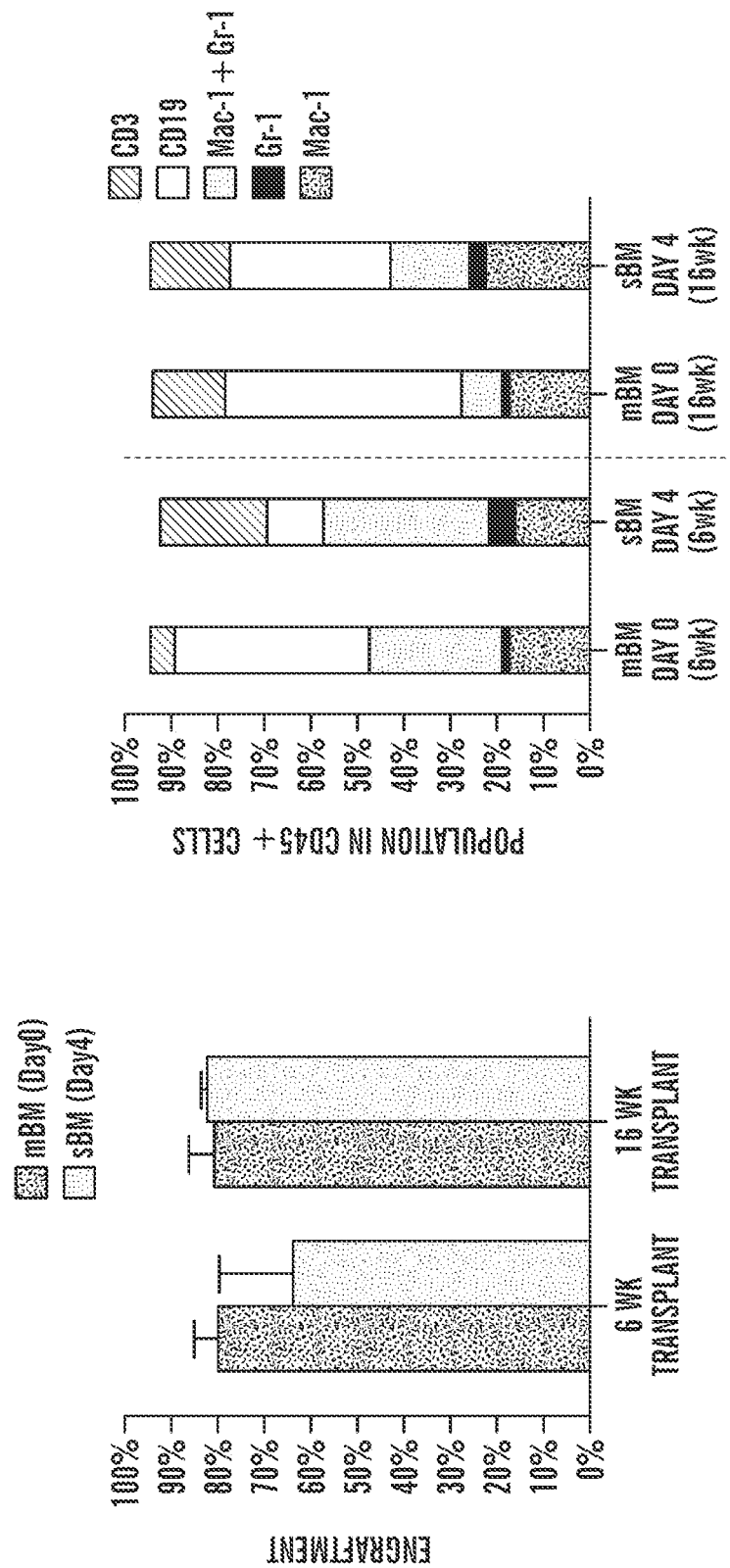

These data suggest that the engineered bone marrow system described herein can maintain a functional hematopoietic niche capable of supporting hematopoietic stem and progenitor cells in vitro; however, to confirm that the engineered marrow remains functional, it is necessary to demonstrate its functionality in vivo. To meet this challenge, cells isolated from engineered marrow after 4 days in culture and from natural marrow freshly isolated from the femur of mice expressing stable green fluorescent protein (GFP) were transplanted into lethally irradiated syngeneic mice. The presence of short-term and long-term HSCs in the engineered bone marrow was assessed by determining the ability of the GFP-labeled marrow cells to reconstitute the cellular components of peripheral blood 6 weeks and 16 weeks after transplantation, respectively. Bone marrow harvested from the device following 4 days in the microfluidic culture system successfully engrafted in the mice at a similar rate as freshly harvested mouse femur bone marrow (FIG. 20A). Following transplantation, the cultured marrow cells successfully produced all lineages of differentiated blood cells in vivo. By 6 and 16 weeks after transplantation, 65% and 85% (respectively) of the blood cells in the recipient were descended from the transplanted cells. These data confirm that the bone marrow that was engineered in vivo as described herein is fully functional bone marrow, and that the engineered marrow cultured within a microfluidic chip is capable of maintaining functional HSCs in vitro.

After 4 weeks implantation, the bone-inducing materials induced the formation of bone inside the device. After 8 weeks implantation, the synthetic bone consists of cortical bone on the outside and trabecular bone on the inside with similar architectural properties to a mouse vertebra (FIGS. 19A-19D).

The bone marrow cells isolated from the synthetic bone marrow after 4 days in the microfluidic culture system were transplanted into lethally irradiated mice. The synthetic bone marrow cells successfully engrafted the mice and populated all lineages of differentiated cells 16 weeks after transplantation (FIGS. 20A-20B). The engraftment rate of the synthetic bone marrow cells 16 week after transplantation is identical to that of the mouse bone marrow cells harvested from a mouse femur, demonstrating that the device described herein is capable of maintaining functional long-term hematopoietic stem cells ex vivo.

Example 9: Human Bone Marrow

The ultimate value of the bone marrow-on-a-chip technology for clinical applications, such as production of blood cells, will depend on the ability to adapt it for use with human hematpoietic cells. To explore this possibility, a mouse bone disk was engineered subcutaneously as described herein and surgically removed from the animal. The internal marrow cavity chip was exposed by cutting a small opening at its edge, and the cavity was flushed with medium to clear it of non-adherent mouse cells after fixing it with paraformaldehyde to retain the niche architecture. Human umbilical cord blood cells (huCBCs) were injected into the engineered bone marrow through the same opening at the edge, which was subsequently sealed using Matrigel. The fixed engineered bone containing huCBCs within its marrow cavity was cultured under flow (1 µL/min, 0.005 dyn/cm$^2$) in a microfluidic device in medium designed to maintain human HSCs. When cells were plated in a standard planar culture dish, flow cytometry analysis revealed that the viability of huCBCs and the number of human HSCs (Lin-CD34+CD38-CD90+ staining cells) in the culture decreased dramatically over 7 days. In contrast, when cultured in the bone marrow microfluidic chip, viability of both huCBCs and human HSCs was maintained for 7 days in vitro (FIGS. 21A-21B). These data indicate that the engineered mouse bone marrow niche retains all of the microenviromental signals required to sustain viability human HSCs in culture, and that the microfluidic chip culture technique can provide a way to sustain and expand these cells in culture for experimental, therapeutic and blood cell manufacturing applications.

There is a need to develop reliable in vitro systems that can reconstitute the complex human bone marrow niche for clinical and scientific purposes. Development of a microdevice that can maintain viability and self-renewing function of short- and long-term HSCs, as well as their ability to differentiate into the various blood cell types would have great value for many applications. Hematopoietic toxicity identified in animal models is a major source of early drug candidate failure during the drug development process; however, animal models are not always predictive of results in humans. Bone marrow chips containing human HSCs and their various lineages can provide an alternative way to test hematopoietic effects of drugs, as well as toxins or radiation exposure, on human marrow before entering clinical trials. They can also provide a way to enhance current bone marrow transplantation techniques by expanding cells isolated from a single clinical bone marrow aspirate to large enough numbers in vitro that they can be frozen and stored to be used for multiple transplants for the same patient in the future.

As blood donor supplies are limited and complicated by infection risk (e.g. HIV), there is also a need for high quality sources of human blood cells (leukocytes, erythrocytes, platelets) for therapeutic applications. Bone marrow chips that can maintain human HSC viability in vitro and enable sustained production of differentiated blood cell types can provide an alternative manufacturing strategy.

Finally, understanding of hematopoietic niche physiology still remains incomplete due to the limited availability of relevant in vitro models that successfully recreate and/or mimic the native bone marrow environment outside of a living animal. The bone marrow chip microtechnology described here provides for creation of an organ-on-a-chip device that reconstitutes a whole functional bone marrow and a permeating trabecular bone matrix, as well as providing a way to culture HSCs and generate various blood lineages in vitro.

```
                         SEQUENCE LISTING

SEQ ID NO: 1 BMP-2 amino acid sequence, NCBI ID NO: NP_001191.1
    1 mvagtrclla lllpqvllgg aaglvpelgr rkfaaassgr pssqpsdevl sefelrllsm
   61 glkqrptps rdavvppyml dlyrrhsgqp gspapdhrle raasrantvr sfhheeslee
  121 etsgkttr rfffnlssip teefitsael qvfreqmqda lgnnssfhhr iniyeiikpa
  181 tanskfpvtr lldtrlvnqn asrwesfdvt pavmrwtaqg hanhgfvvev ahleekqgvs
  241 krhvrisrsl hqdehswsqi rpllvtfghd gkghplhkre krqakhkqrk rlkssckrhp
  301 lyvdfsdvgw ndwivappgy hafychgecp fpladhlnst nhaivqtlvn svnskipkac
  361 cvptelsais mlyldenekv vlknyqdmvv egcgcr SEQ ID NO: 2 BMP-4 amino acid sequence, NCBI ID NO: NP_001193,
NP_570911, and NP_570912
    1 mipgnrmlmv vllcqvllgg ashaslipet gkkkvaeiqg haggrrsgqs hellrdfeat
   61 llqmfghrr pqpsksavip dymrdlyrlq sgeeeeeqih stgleyperp asrantvrsf
  121 hheehlenip gtsensafrf lfnlssipen evissaelrl freqvdqgpd wergfhrini
  181 yevmkppaev vpghlitrll dtrlvhhnvt rwetfdvspa vlrwtrekqp nyglaievth
  241 lhqtrthqgq hvrisrslpq gsgnwaqlrp llvtfghdgr ghaltrrrra krspkhhsqr
  301 arkknkncrr hslyvdfsdv gwndwivapp gyqafychgd cpfpladhln stnhaivqtl
  361 vnsvnssipk accvptelsa ismlyldeyd kvvlknyqem vvegcgcr
```

What is claimed herein is:

1. A method for producing bone marrow tissue, the method comprising implanting a microfluidic implantation device comprising at least one of:
   demineralized bone powder; and
   a bone morphogenic protein (BMP)
   in a subject under conditions whereby bone marrow tissue forms in the microfluidic implantation device;
   removing the microfluidic implantation device and the bone marrow tissue contained in the microfluidic implantation device from the subject;
   providing a perfusion fluid to the bone marrow tissue to maintain the bone marrow tissue ex vivo;
   wherein the microfluidic implantation device includes at least one cell growth chamber and at least one open port providing a passage to the cell growth chamber to enable cells to enter the cell growth chamber after said implanting.

2. The method of claim 1, further comprising the step of removing the tissue from the microfluidic implantation device prior to providing perfusion fluid.

3. The method of claim 2, further comprising the step of placing the tissue in a microfluidic system prior to providing perfusion fluid.

4. The method of claim 1, wherein providing a perfusion fluid comprises connecting the microfluidic implantation device to a microfluidic system.

5. The method of claim 4, wherein the microfluidic implantation device includes at least one fluid channel separated from the at least one cell growth chamber by a porous separation component.

6. The method of claim 5, wherein the microfluidic implantation device includes at least one inlet port and at least one outlet port connecting the at least one fluid channel to the microfluidic system and providing perfusion fluid to the at least one cell growth chamber through the porous separation component.

7. The method of claim 1, wherein the microfluidic implantation device is implanted such that at least one port faces the muscle tissue of the subject.

8. The method of claim 1, wherein the implantation is subcutaneous, intraperitoneal, or intramuscular.

9. The method of claim 1, wherein the implantation is subcutaneous.

10. The method of claim 1, wherein the bone marrow tissue contained in the microfluidic implantation device comprises hematopoietic cells.

11. The method of claim 1, wherein the bone marrow tissue maintained ex vivo comprises hematopoietic cells.

12. The method of claim 11, wherein the hematopoietic cells are administered to a subject.

13. The method of claim 12, wherein the subject has a condition selected from the group consisting of:
   a compromised immune system; a cancer; an auto-immune disease; radiation toxicity; and a hematopoietic disease.

14. The method of claim 12, wherein the subject has undergone chemotherapy and/or radiation therapy.

15. The method of claim 11, wherein the hematopoietic cells are provided to another tissue type being maintained in vitro.

16. The method of claim 11, wherein the hematopoietic cells are selected from the group consisting of:
   red blood cells; white blood cells; platelets; hematopoietic stem cells; lymphocytes; eosinophils; neutrophils; monocytes; a hematopoietic progenitor cell; and a mixture of two or more of these cell types.

17. The method of claim 1, wherein said implantation device contains both demineralized bone powder and one or more bone morphogenic proteins (BMPs).

18. A method for producing bone marrow tissue, the method comprising implanting a microfluidic implantation device comprising:
   demineralized bone powder;
   bone-morphogenic protein 2 (BMP-2);
   bone-morphogenic protein 4 (BMP-4); and
   type I collagen;
   in a subject under conditions whereby bone marrow tissue forms in the microfluidic implantation device;
   removing the microfluidic implantation device and the bone marrow tissue contained in the microfluidic implantation device from the subject;
   providing a perfusion fluid to the bone marrow tissue to maintain the bone marrow tissue ex vivo;
   wherein the microfluidic implantation device includes at least one cell growth chamber and at least one open port providing a passage to the cell growth chamber to enable cells to enter the cell growth chamber after said implanting.

* * * * *